United States Patent
Potts et al.

(10) Patent No.: US 8,807,090 B1
(45) Date of Patent: Aug. 19, 2014

(54) SUPPORT KIT, GARMENT AND METHOD OF USING SAME

(71) Applicants: Maria Paola Mangini Potts, Escondido, CA (US); Jerry Richard Potts, Escondido, CA (US)

(72) Inventors: Maria Paola Mangini Potts, Escondido, CA (US); Jerry Richard Potts, Escondido, CA (US)

(73) Assignee: Potts-Mangini Trust of October 15, 2002, Escondido, CA (US)

( * ) Notice: Subject to any disclaimer, the term of this patent is extended or adjusted under 35 U.S.C. 154(b) by 0 days.

(21) Appl. No.: 13/915,090

(22) Filed: Jun. 11, 2013

(51) Int. Cl.
*A01K 13/00* (2006.01)
*A01K 29/00* (2006.01)
*A01K 23/00* (2006.01)

(52) U.S. Cl.
CPC ............... *A01K 23/00* (2013.01); *A01K 29/00* (2013.01)
USPC .......................................................... 119/850

(58) Field of Classification Search
USPC ........ 119/850, 856, 858, 863; 2/79, 102, 114, 2/400, 403, 406, 227, 228, 69
IPC ...................................................... A01K 13/00
See application file for complete search history.

(56) References Cited

U.S. PATENT DOCUMENTS

| | | | |
|---|---|---|---|
| 798,320 A | 8/1905 | Carli | |
| 1,595,834 A | 8/1926 | Griffiths | |
| 1,611,420 A * | 12/1926 | Cuddy | 2/79 |
| 4,527,991 A | 7/1985 | Msarsa | |
| 4,813,949 A | 3/1989 | O'Rourke | |
| 4,955,880 A * | 9/1990 | Rodriquez | 604/393 |
| 4,987,610 A * | 1/1991 | Hunt | 2/46 |
| 4,996,949 A | 3/1991 | Wunderman et al. | |
| 5,005,525 A | 4/1991 | Stanton | |
| 5,146,874 A * | 9/1992 | Vidal | 119/868 |
| 5,184,762 A | 2/1993 | Nevitt | |
| D334,252 S | 3/1993 | Stubbs | |
| 5,226,386 A | 7/1993 | Thoma | |
| 5,355,836 A | 10/1994 | Vallery | |
| D363,572 S | 10/1995 | Obenchain | |
| 5,463,985 A * | 11/1995 | Shover | 119/850 |
| 5,555,847 A | 9/1996 | Kelly | |
| 5,582,605 A * | 12/1996 | Lepie | 604/385.06 |
| 5,632,235 A | 5/1997 | Larsen et al. | |
| D379,687 S | 6/1997 | Curtis | |
| 5,640,715 A * | 6/1997 | Adams | 2/46 |
| 5,644,902 A | 7/1997 | Kemp | |
| D383,255 S | 9/1997 | Caditz | |
| D384,780 S | 10/1997 | McLaughlin | |
| 5,813,369 A | 9/1998 | Fujinaga | |
| 5,887,772 A | 3/1999 | Dooley | |
| 5,937,795 A | 8/1999 | Raphael | |
| 5,996,537 A | 12/1999 | Caditz | |
| D429,390 S | 8/2000 | Grady et al. | |
| 6,142,105 A | 11/2000 | McKnight | |
| 6,234,117 B1 * | 5/2001 | Spatt | 119/850 |
| 6,368,313 B1 * | 4/2002 | Howard | 604/385.09 |
| D457,988 S | 5/2002 | Kerrigan | |
| 6,394,041 B1 | 5/2002 | Katz | |
| 6,557,497 B1 | 5/2003 | Milligan | |

(Continued)

*Primary Examiner* — David Parsley
*Assistant Examiner* — Thien Thanh Pham
(74) *Attorney, Agent, or Firm* — Jerry R. Potts

(57) ABSTRACT

A self contained support kit includes a utility envelope which is adapted to be removably secured to an animal protective garment, such as a sweater or shirt, for the deployment of a support coupler to grip and hold a diaper in its intended protective position.

17 Claims, 15 Drawing Sheets

(56) References Cited

U.S. PATENT DOCUMENTS

| | | |
|---|---|---|
| 6,571,745 B2 | 6/2003 | Kerrigan |
| 6,637,367 B1 | 10/2003 | Dost et al. |
| 6,675,745 B1 | 1/2004 | Brewington |
| 7,044,087 B1 | 5/2006 | Brecheen |
| 7,753,008 B2 | 7/2010 | Krenkel |
| 7,918,192 B1 | 4/2011 | Digh et al. |
| 8,291,867 B2 | 10/2012 | Blizzard |
| 8,302,565 B2 | 11/2012 | Williams |
| 2004/0030311 A1* | 2/2004 | Suzuki et al. ............... 604/367 |
| 2005/0028755 A1* | 2/2005 | Le Fevre ...................... 119/868 |
| 2006/0253953 A1* | 11/2006 | Williams ............................ 2/69 |
| 2007/0032769 A1* | 2/2007 | Cohen et al. ............. 604/385.06 |
| 2010/0031898 A1* | 2/2010 | Page ............................. 119/850 |
| 2011/0192357 A1 | 8/2011 | Pellegrini |
| 2012/0117715 A1* | 5/2012 | Weafer ............................. 2/228 |

\* cited by examiner

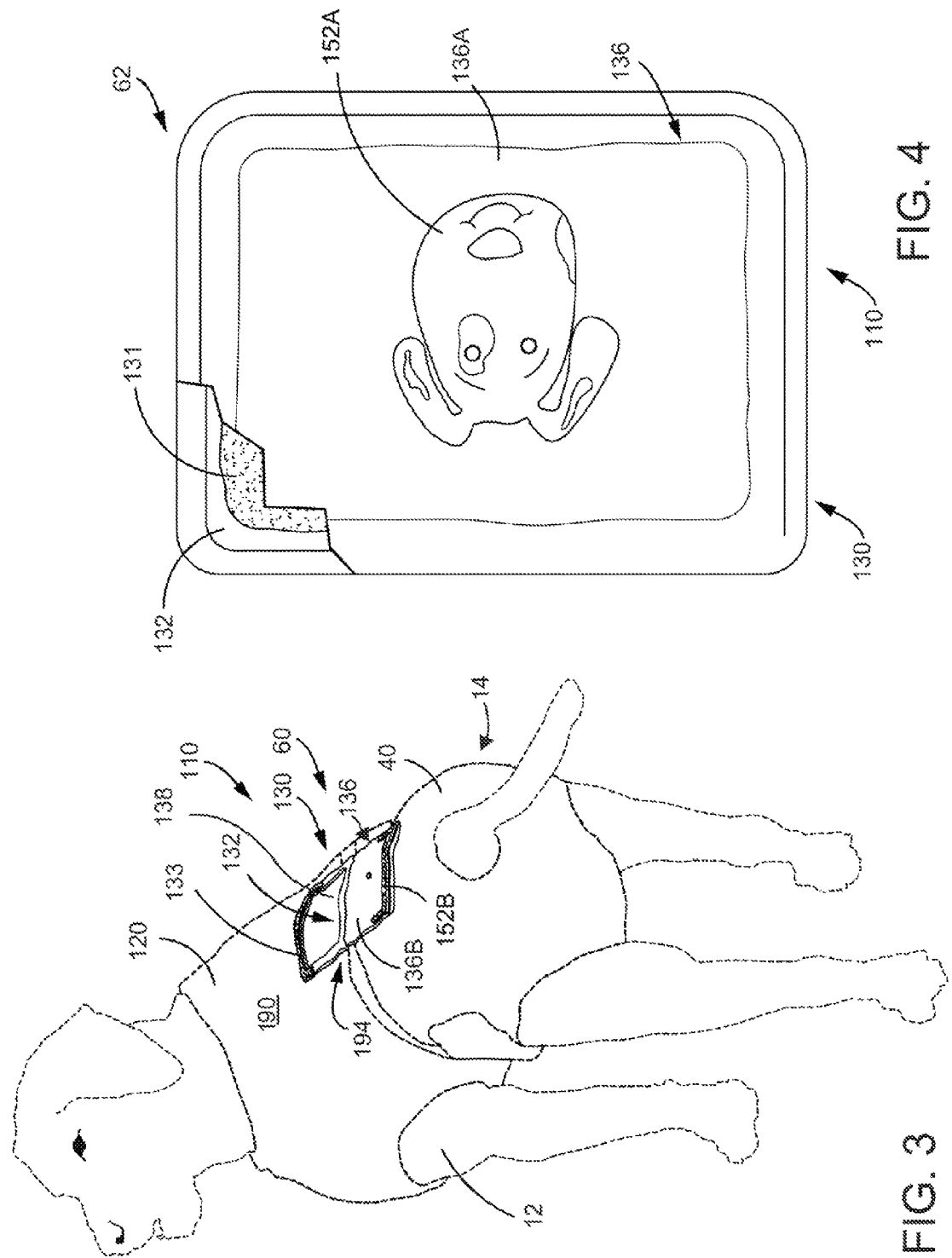

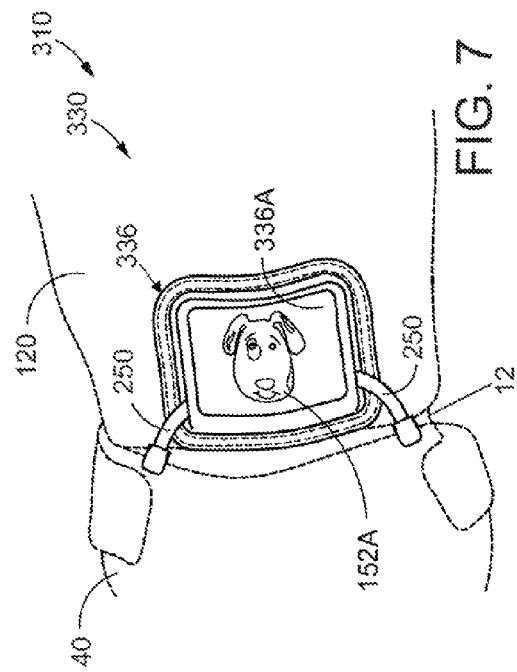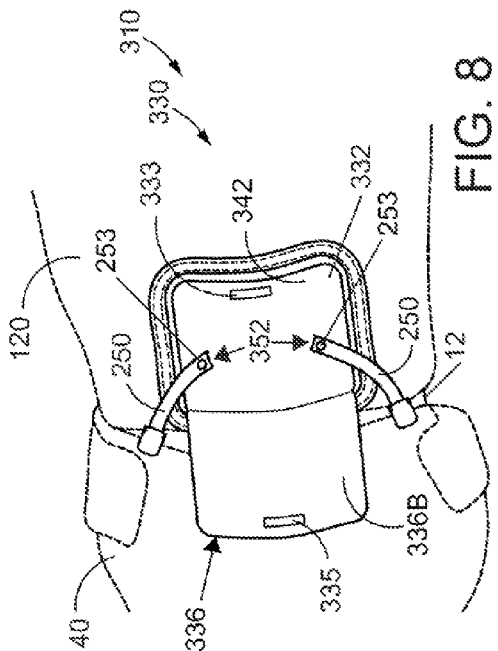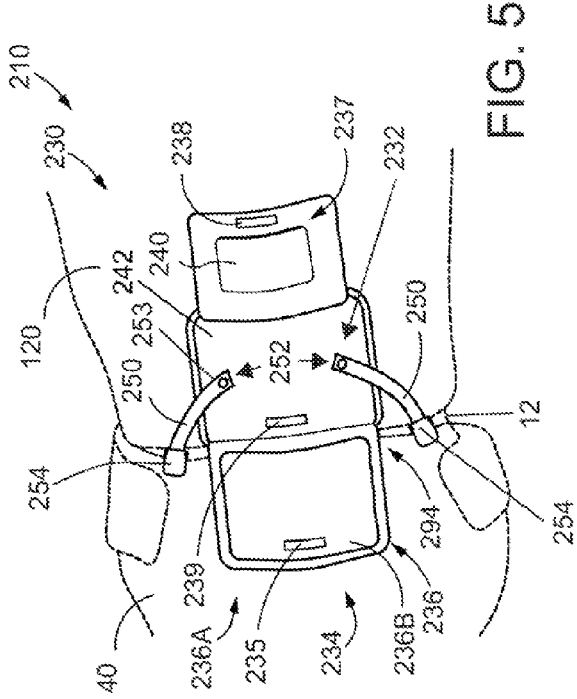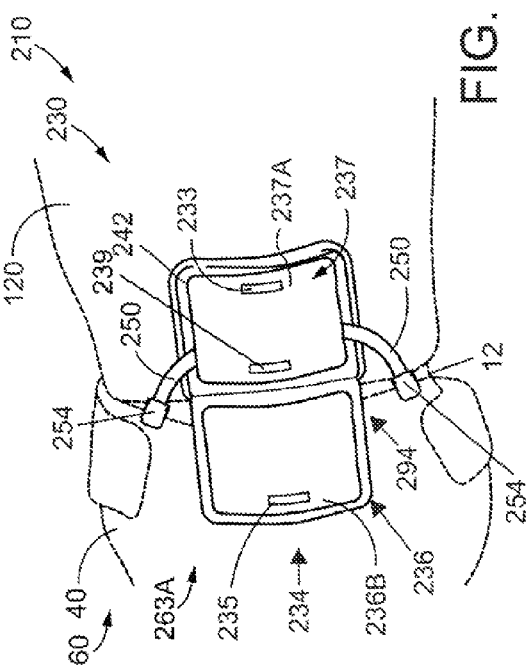

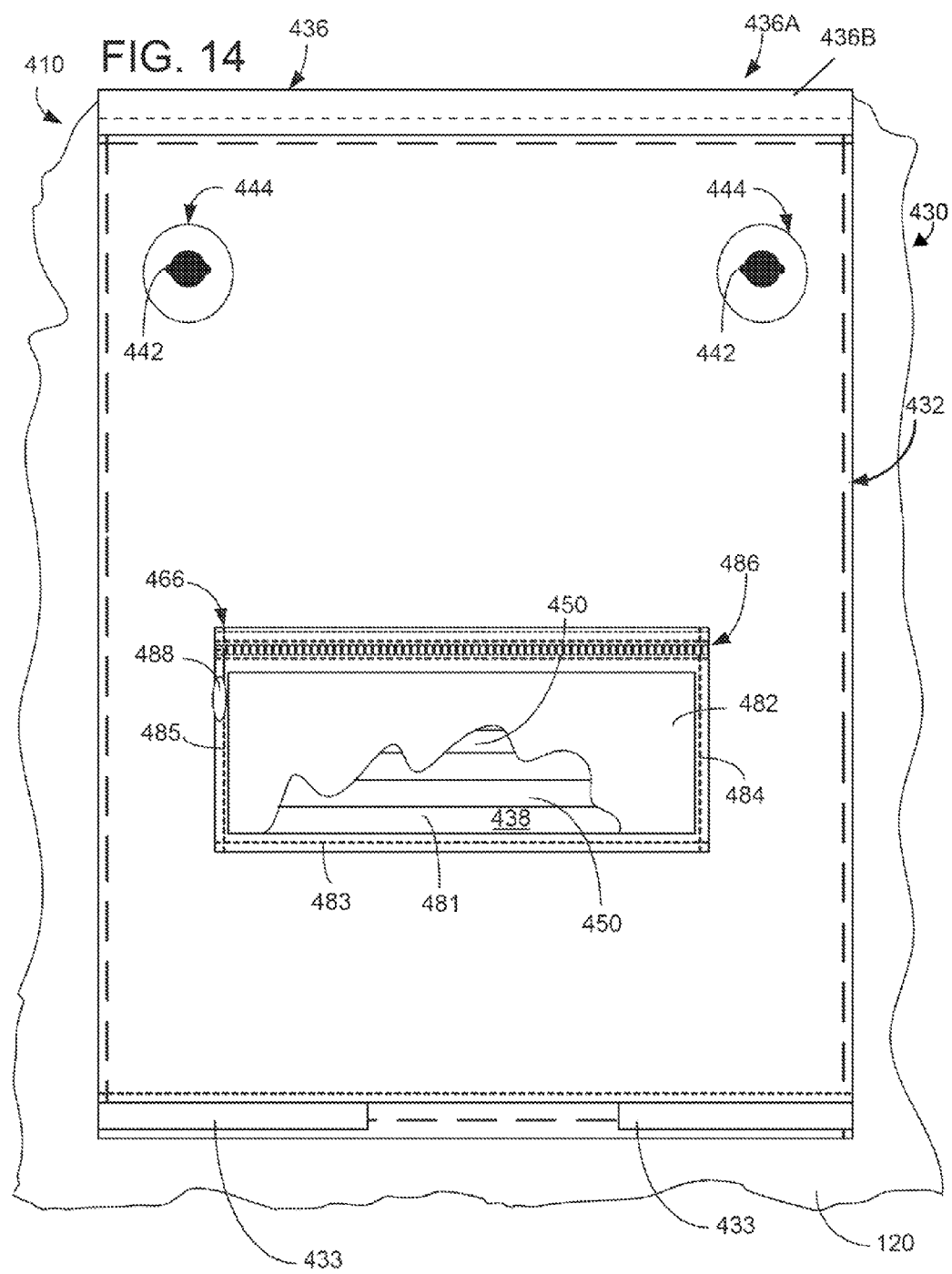

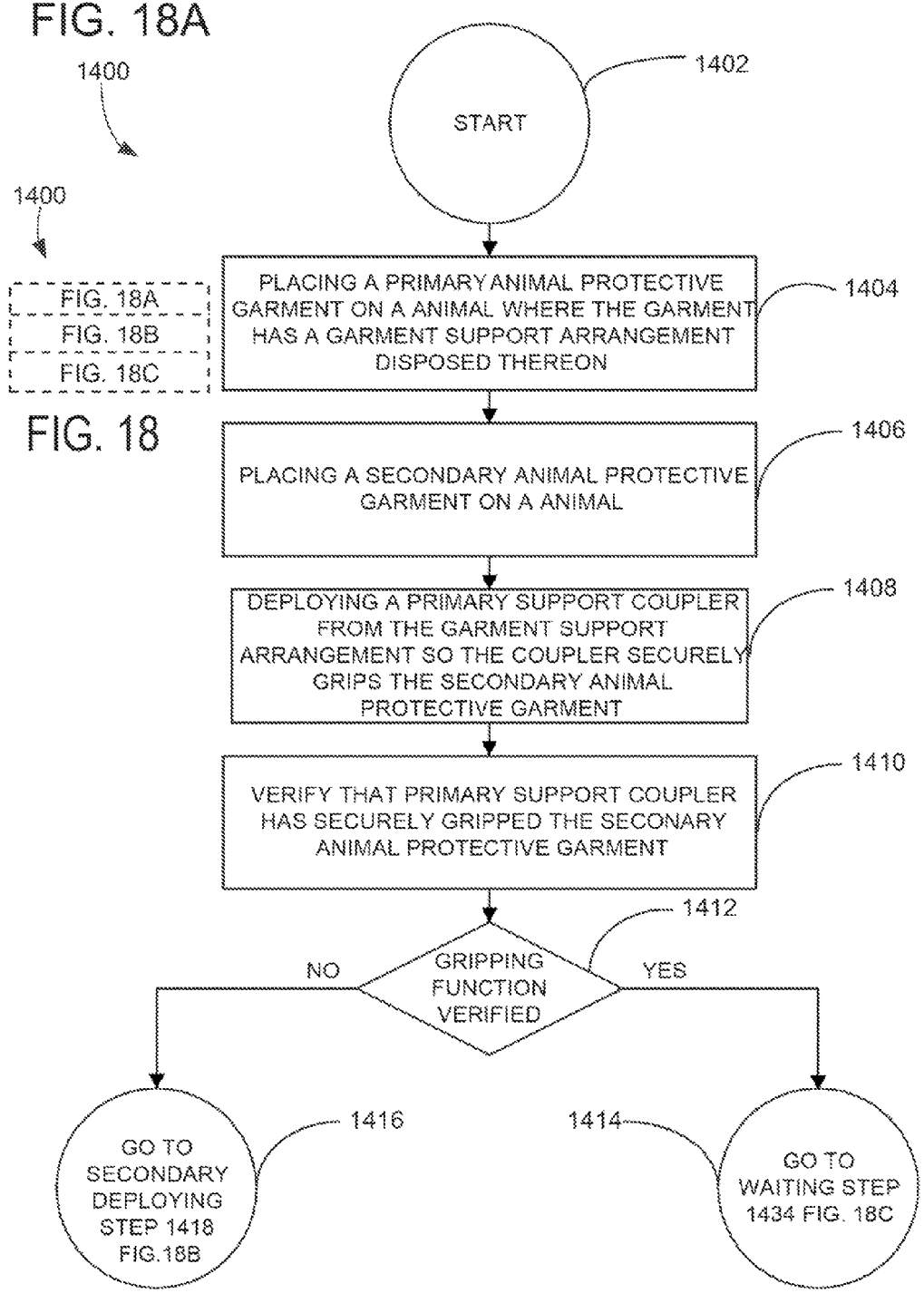

SUPPORT KIT, GARMENT AND METHOD OF USING SAME

FIELD OF THE INVENTION

This invention relates generally to animal garments and more particularly to an animal support garment and support garment kit and methods of using the garment and kit for helping to maintain an animal diaper or shield in a desired animal protection position while being worn by an animal.

BACKGROUND OF THE INVENTION

Utilization of dog and cat diapers is well known in the prior art. For example, reference may be made to the following U.S. Pat. No. 4,813,949 by O'Rourke issued on Mar. 21, 1989; U.S. Pat. No. 5,234,421 by Lowman issued on Feb. 10, 1993; U.S. Pat. No. 5,954,015 by Ohta issued on Sep. 21, 1999; U.S. Pat. No. 5,463,985 by Shover issued on Nov. 7, 1995; U.S. Pat. No. 5,555,847 by Kelly issued on Sep. 17, 1996; and US Patent Application Publication No.: 2011/0192357 by Pellegrini published on Aug. 11, 2011.

While each of the above-mentioned diapers have generally been satisfactory for their intended purpose, nevertheless they have not been entirely satisfactory. That is, due to the body shape of the rear hind portion of a dog or cat, many of the conventional animal diapers will not remain in place on the animal but instead, will slip and slide off the rear of the animal. This is true whether or not the diaper is soiled, but it is particularly true when the absorbent material within such a diaper becomes saturated with the urine and waste product of the animal. In either event, either the clean or the spent diaper may fall off the animal leaving the animal unprotected from soiling and causing unwanted and undesired damage to an indoor environment area or otherwise protected area where animal urine and waste product discharge is undesired and unwanted.

Recognizing this slippage problem, various solutions have been proposed in the form of improved diaper constructions and diaper support systems. For example, reference may be made to the following U.S. Pat. No. 6,142,105 by McKnight issued on Nov. 7, 2000; U.S. Pat. No. 7,753,008 by Krenkel issued on Jul. 13, 2010; and U.S. Pat. No. 8,302,565 by Williams issued on Nov. 6, 2012.

Each of the above mentioned diaper support garments and harnesses have been generally satisfactory for their general intended purpose; nevertheless, they have not been entirely satisfactory. In this regard, if the animal owner desires to release his or her animal to an outside environment area for the purpose of eliminating their waste products, the support garment and diaper must be removed from the animal and then subsequently the diaper and the support garment must be placed once again on the animal, which is not only time consuming and inconvenient but may also because of such nuisance encourage the animal owner to leave a soiled diaper on the animal for an excessive period of time.

Therefore it would be highly desirable to have a new and improved diaper support system that prevents a soiled animal diaper from sliding off the animal either because of normal animal activity movement or because of excess diaper weight caused when the absorbent material within the diaper becomes saturated with the waste product of the animal.

It would also be highly desirable to have a new and improved diaper support system that does not require the support system to be removed from the animal when the animal is released to an outside environment for waste elimination purposes thereby encouraging the animal owner to release the animal to the outside environment on a more frequent basis.

Such a new and improved diaper support system should be universal and easy and convenient to use with animals of different breeds and sizes as well as with the various different types and kinds of utilized animal diapers. Finally, such a new and improved diaper support system should be relatively inexpensive and convenient to use with conventional animal protective and decorative clothing items like sweaters, T-shirts and the like.

SUMMARY OF THE INVENTION

In accordance with one aspect of the present invention there is provided a support garment for an animal that comprises a base animal protective garment having disposed thereon a garment support arrangement that helps secure a primary animal protective garment or diaper in a desired animal protective position. The garment support arrangement includes a utility envelope that defines at least one compartment for the storage and release of a support coupler, where the support coupler is adapted to be removably secured to the diaper for helping to maintain the diaper in its intended desired animal protective position.

In one embodiment of the first aspect of the present invention the base animal protective garment and the diaper have separate and distinctly different animal protection purposes and are adapted to be spaced from one another on an animal to be protected.

In another embodiment of the first aspect of the present invention the utility envelope of the garment support arrangement has a closure flap for protecting the support coupler from an animal wearing the animal protective garment.

In yet another embodiment of the present invention the utility envelope is adhesively secured to the animal protective garment.

In still yet another embodiment of the present invention the utility envelope is sewn to the animal protective garment.

In yet another embodiment of the present invention the utility envelope is secured by rivets to the animal protective garment.

In another embodiment of the present invention the garment support arrangement includes a reinforcement pad that helps to prevent the tearing and ripping of the garment support arrangement under repeated use.

Another embodiment of the present invention is that the support coupler is a set of hooks or a set of loops that are adapted to releasably engage a fabric surface of the diaper so that the diaper is maintained in its intended desired animal protective position.

In another embodiment of the present invention the set of hooks or said set of loops is disposed on a distal end portion of an elastic band where a proximal end portion of the elastic band is secured to the reinforcement pad.

In still yet another embodiment of the present invention the support coupler is a large loop having a sufficiently large opening to receive therein at least one set of securing members forming part of the diaper so that the diaper is maintained in its intended desired animal protective position.

In yet another embodiment of the present invention the large loop is disposed on a distal end portion of an elastic band; and wherein a proximal end portion of the elastic band is secured to the reinforcement pad.

In another embodiment of the present invention the support coupler is a fastener for engaging a fabric surface of the diaper.

In still yet another embodiment of the present invention the fastener is a clip.

In another embodiment of the present invention the clip is a clam shaped clip.

In still yet another embodiment of the present invention the clip is an alligator clip.

In yet another embodiment of the present invention the fastener is disposed on a distal end portion of an elastic band; and wherein a proximal end portion of the elastic band is secured to the reinforcement pad.

In still yet another embodiment of the present invention the fastener is a Y-shaped fastener that includes a pair of short straight leg members forming a V like configuration and a single long straight leg member having a distal end and a proximal end; wherein the distal end of the single long straight leg member intersects an interconnection between the pair of short straight leg members and wherein a proximal end of the long straight leg is secured to the reinforcement pad; and wherein the pair of short straight leg members have a set of hooks or a set of loops disposed thereon for engaging opposing fabric surfaces of the diaper.

In accordance with a second aspect of the present invention a garment support kit for an animal protective garment comprises a garment support arrangement to facilitate securing a diaper so the diaper is maintained in its intended and desired animal protective position; and wherein the garment support arrangement is adapted to be secured to the animal protective garment to facilitate deployment of a support coupler so that the support coupler can be coupled to the diaper helping to maintain the diaper in its intended desired animal protective position.

An embodiment of the second aspect of the present invention is that the garment support arrangement includes a utility envelope having a closure flap, where the envelope has at least one compartment dimensioned for containing therein the support coupler to facilitate removably securing the animal protective garment to the diaper to help maintain the diaper in its intended desired animal protective position.

Another embodiment of the second aspect of the present invention that the envelope is adapted to be adhesively secured to said animal protective garment.

Yet another embodiment of the second aspect of the present invention is the provision that the closure flap is adapted to be positioned in either an open position or a close position; wherein the closure flap when positioned in the open position, facilitates the deployment of the support coupler from the at least one compartment so that the support coupler can be fastened to the diaper to releasably hold the diaper in its intended desired animal protective position; and wherein the closure flap when positioned in its closed position facilitates the protection of the support coupler from an animal wearing the animal protective garment.

In still yet another embodiment of the second aspect of the present invention is the primary animal protective garment and the diaper garment have separate and distinctly different animal protection purposes and are spaced from one another when disposed on an animal to be protected.

In another embodiment of the second aspect of the present the garment support arrangement is an elongate flap that has a proximal end and a distal end, wherein the proximal end is adapted to be permanently secured to the animal protective garment and wherein a distal end portion of the flap is provided with a set of hooks or a set of loops for engaging a fabric surface of the diaper to releasably hold the diaper in its intended desired animal protective position.

In yet another embodiment of the second aspect of the present the flap has a top surface and a bottom surface; wherein the top surface has disposed thereon along its longitudinal dimension at least one strip of hooks or at least one strip of loops to facilitate the rolling up of the flap into a cylindrical configuration when said flap is not in use; wherein the set of hooks or the set of loops for engaging said fabric surface of the diaper is disposed on the bottom surface of the flap; and wherein the flap in its cylindrical configuration is adapted to be rolled open into a substantially flat configuration for deployment and engagement with the fabric surface of the diaper when in use.

In still yet another embodiment of the second aspect of the present invention is that the utility envelope includes a reinforcement pad to help prevent the tearing and ripping of the animal protective garment.

Yet another embodiment of the second aspect of the present the support coupler is a set of hooks or a set of loops for releasably engaging a fabric surface of the diaper so that the diaper is maintained in its desired animal protective position.

Another embodiment of the second aspect of the present the set of hooks or the set of loops is disposed on a distal end portion of a fabric band; and wherein a proximal end portion of the fabric band is secured to the reinforcement pad.

In yet another embodiment of the second aspect of the present the support coupler is a large loop having a sufficiently large opening to receive therein at least one set of securing members forming part of the diaper so that the diaper is maintained in its desired animal protective position.

In still yet another embodiment of the second aspect of the present invention the large loop is disposed on a distal end portion of a fabric band; and wherein a proximal end portion of the fabric band is secured to the reinforcement pad.

An embodiment of the second aspect of the present invention the support coupler is an elongate flap having a proximal end and a distal end; wherein said proximal end is adapted to be permanently secured within the utility envelope and wherein a distal end portion of the flap is provided with a set of hooks or a set of loops for engaging a fabric surface of the diaper to releasably hold it in its intended animal protective position.

In another embodiment of the second aspect of the present invention the flap has a top surface and a bottom surface; wherein the top surface has disposed thereon along its longitudinal dimension at least one strip of hooks or at least one strip of loops to facilitate the rolling up of the flap into a tight cylindrical configuration for storage within the envelope when the flap is not in use; wherein the set of hooks or the set of loops for engaging the fabric surface of the diaper is disposed on the bottom surface of the flap; and wherein the flap in its cylindrical configuration is adapted to be rolled open into a substantially flat configuration for deployment from the envelope and for engagement with the fabric surface of the diaper when in use.

In accordance with a third aspect of the present invention a garment support kit for an animal protective garment comprises a garment support arrangement to facilitate securing a diaper to the animal protective garment to ensure that diaper remains secured in a desired and intended animal protective position; wherein the garment support arrangement includes: a support coupler adapted to be coupled to the diaper to help maintain the diaper in its desired and intended animal protective position; and a reinforcement pad adapted to be permanently secured to the animal protective garment as a fabric reinforcement to help prevent the tearing and ripping of the animal protective garment and for supporting from below for deployment the support coupler.

BRIEF DESCRIPTION OF DRAWINGS

The above mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 3 is a perspective view of a self contained diaper support kit which kit is constructed in accordance to the present invention, illustrating the diaper support kit supporting a dog diaper;

FIG. 4 is a top plane view of the self contained diaper support kit of FIG. 3, illustrating the diaper support kit in a closed non-diaper supporting position;

FIG. 5 is a top plane view of another self contained diaper support kit having a two compartment construction with a plurality of deployed support couplers, which kit is constructed in accordance with the present invention;

FIG. 6 is a top plane view of the diaper support kit of FIG. 5, illustrating deployed primary and secondary support couplers supporting a diaper, with the secondary support coupler being secured by a closure flap to help retain the diaper in an intended animal protective position;

FIG. 7 is a top plane view of another diaper support garment having a single compartment construction with a plurality of plural support couplers, which garment is constructed in accordance with the present invention;

FIG. 8 is a top plane view of the diaper support garment of FIG. 7, illustrating deployed primary and secondary support couplers supporting a diaper;

FIG. 14 is a top plane view of still another self diaper support garment, which is constructed in accordance with the present invention;

FIG. 18 is a flowchart illustrating a novel method of using a support garment to engage, support and retain an animal diaper or an animal shield in its intended and desired animal protective position;

FIGS. 18A-C are flowcharts forming part of the flowchart of FIG. 18, illustrating the novel method of using a support garment to engage, support and retain an animal diaper or an animal shield in its intended and desired animal protective position;

DETAILED DESCRIPTION OF PREFERRED EMBODIMENTS

Figure 1:
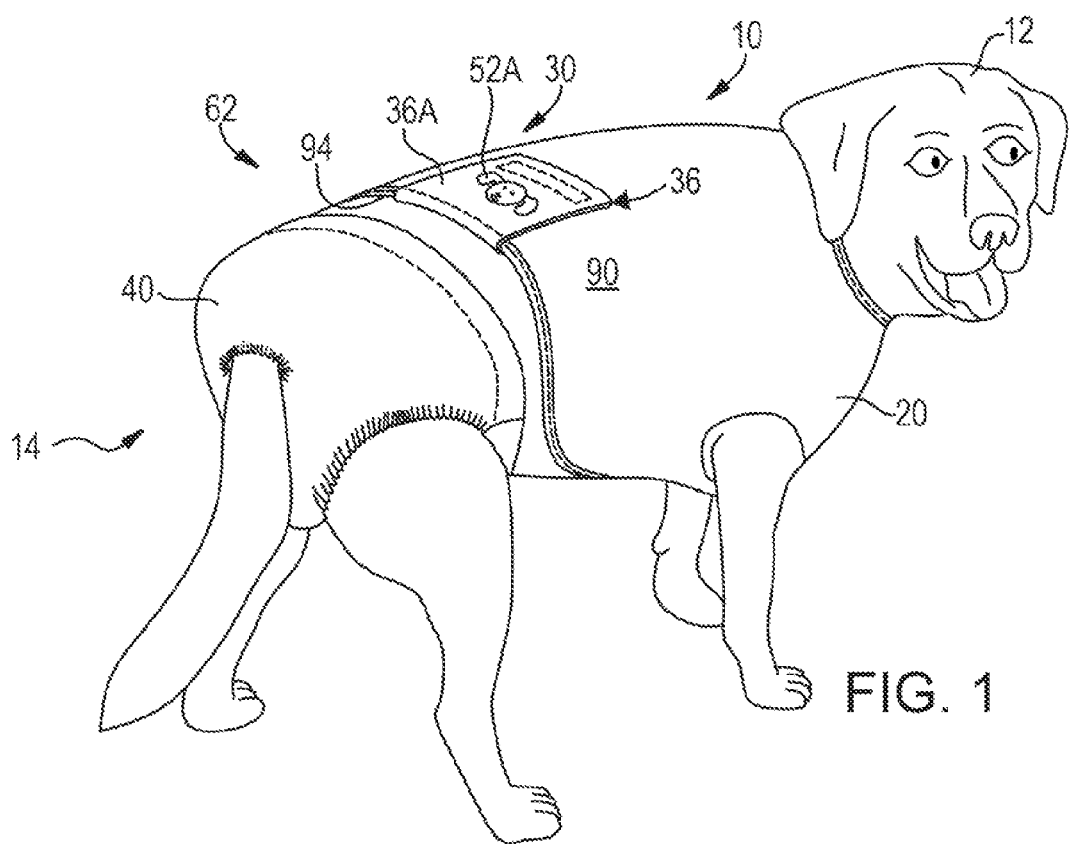
FIG. 1 is a perspective view of a diaper support garment which is constructed according to the present invention illustrating the support garment being worn in combination with a dog diaper.
Figure 2:
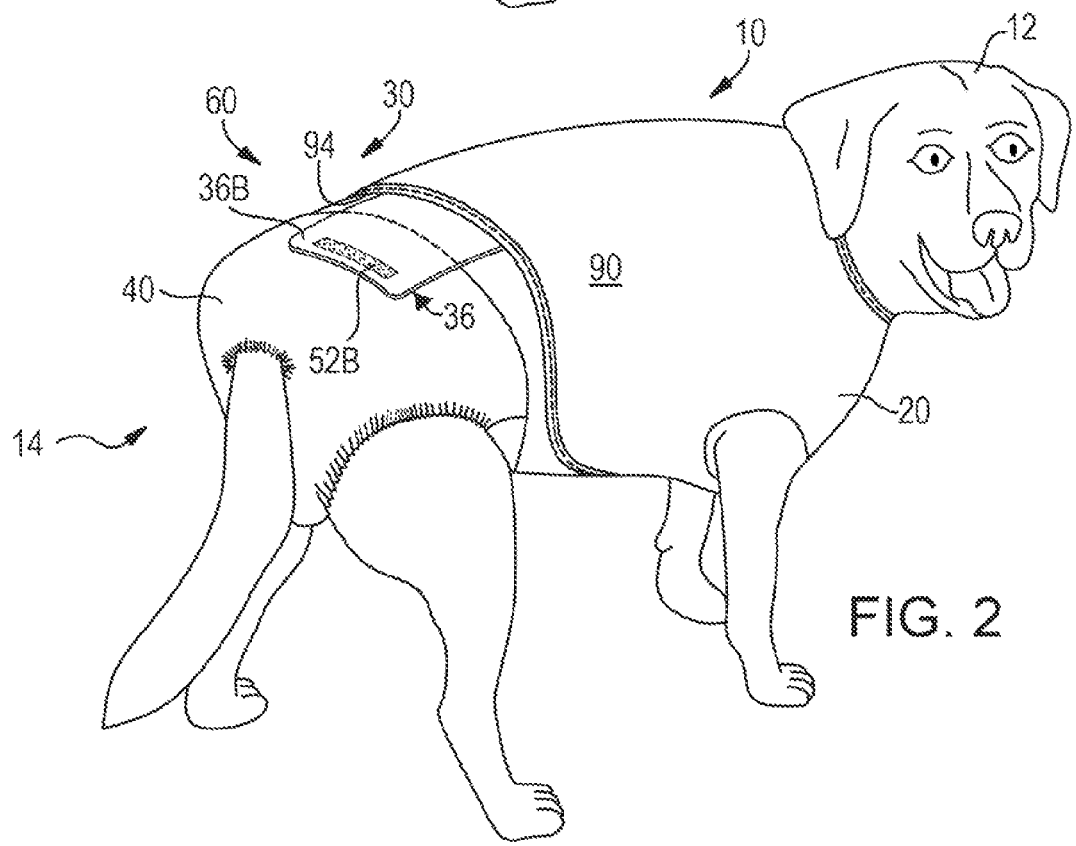
FIG. 2 is a perspective view of the diaper support garment of FIG. 1, illustrating the diaper support garment supporting the dog diaper.
Figure 18B:
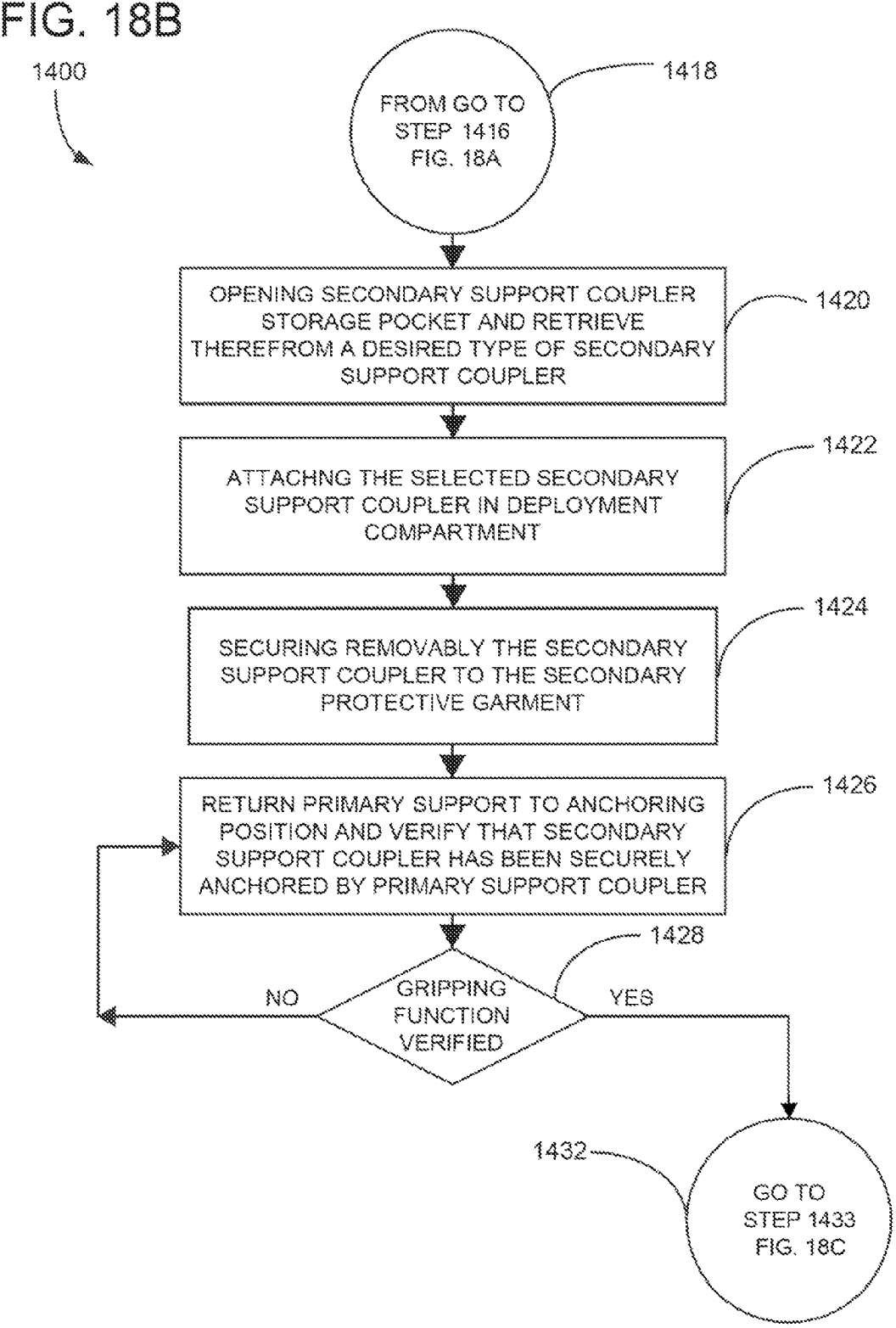

Referring now to the drawings and more particularly to FIGS. 1-2, a multi-purpose pet protection garment according to one exemplary embodiment of the present invention is illustrated and shown generally at reference character 10. The pet protection garment 10, when used in accordance with a novel method of use 1400 (FIG. 18), functions to grip and securely hold a secondary animal protection garment, such as a diaper or shield 40, in its intended and desired animal protective position, even though the diaper 40 may be fully loaded or completely saturated with animal waste product. The protection garment 10 also sufficiently grips and holds the diaper 40 when it is being worn by an older animal whose back may be so severely slanted that it would be difficult, if not impossible, to otherwise securely hold the diaper 40 in its intended and desired animal protective position due to undesired and unwanted diaper slippage.

In accordance with the novel method of using 1400 as best seen in FIG. 18, the pet protection garment 10, several unique and novel advantages are obtained or achieved. One advantage is that the pet protection garment 10 prevents a soiled animal diaper 40 from accidentally sliding off an animal 12 either because of normal animal activity movements or because of excessive diaper weight caused when the absorbent material within the diaper 40 becomes saturated with the waste product of the animal 12.

Another important advantage of the pet protection garment 10 is that it may be coupled or attached to an animal diaper 40 in a very fast and convenient manner, as best seen in FIG. 2, so the diaper 40 may be held in its intended and desired animal protection position. Likewise, the pet protection garment 10 may be easily and quickly detached from such a diaper 40, as best seen in FIG. 1, permitting the diaper 40 to be quickly and conveniently removed from the animal 12 so that it may be replaced if soiled, or simply removed and temporarily set aside for later use, when the animal 12 is released to a suitable environment for waste elimination purposes. Moreover, the pet protection garment 10 may be worn by a dog or cat or nearly any other type of animal with a similar body construction to that of a dog or cat.

Still yet another advantage of the pet protection garment 10 is that it is universal in nature. That is, the pet protection garment 10 may be utilized to support various different types and kinds of diapers and shields. Still yet another advantage is that the pet protection garment 10 is relatively inexpensive and may be easily and conveniently used for any of its intended purposes whether this is its primary purpose of providing protection to the animal from environmental elements, such as inclement weather conditions or a secondary purpose such as supporting or holding the diaper 40 in its intended and desired animal protection position.

As best seen in FIGS. 1-2, the pet protection garment 10, generally comprises: (1) a primary animal protective garment 20, such as a protective animal vest, a pressure wrap garment, an animal T-shirt, or an animal sweater, and (2) an integrally formed secondary garment support arrangement 30, which is adapted to couple the primary animal protective garment 20 to the secondary animal protective garment 40 in order to secure the secondary animal protective garment 40 in its desired and intended animal protection position. The secondary garment support arrangement 30 is integral to and carried by the primary animal protective garment 20 until it is ready to be deployed for engagement with the secondary animal protective garment 40.

The primary animal protective garment 20 is a multi-function garment; that is, it functions to protect the animal 12 from environmental conditions or it may be configured with simple or complex fabric design features so that it further functions as a decorative fashion wear item or a fashion statement item worn by the animal 12. More particularly, the primary animal protective garment 20 may comprise a water-repellant fabric to protect the animal from raining weather, a thick quilted fabric to protect the animal from cold weather or a lightweight print fabric arranged in a highly decorative pattern. Other fabric structures and primary animal protective garment purposes are clearly contemplated relative to the present invention, so there is no intention of limiting the fabrics or the purpose of the primary protective garment to those mentioned herein.

Considering now the garment support arrangement 30 in greater detail with reference to FIGS. 1-2, the garment support arrangement 30 is composed of a fabric material that is soft, pleasing to the touch, and decorative with an aesthetic appearance which enhances the overall decorative features of the primary animal protective garment 20. In this regard, the support arrangement 30 is integral to the protective garment 20 extending from a distal end 94 portion of the garment 20 rearwardly toward the tail or rear bodily area 14 of the animal 12 providing the primary support garment 20 with a decorative tail 36 (FIG. 2). The decorative tail 36 has a sufficient length dimension and a sufficient width dimension to overlay a substantial top surface, proximal end area, of the diaper 40 when the tail 36 of the support arrangement 30 is disposed in an open or diaper engaging position, indicated generally at 60 as best seen in FIG. 2.

Because of its fabric construction, the garment support arrangement 30 is integrally formed in the fabric structure of the animal protective garment 20 at about a distal end area 94 thereof. In this regard, the decorative garment 20 may be cut, constructed, sewn and fashioned to enhance the decorative features of the protective garment 20 while at the same time enabling the protective garment 20 to have a further unique function, namely being constructed via the tail 36 to grip and hold a diaper in its desired and intended animal protection position. In the alternative, the support arrangement 30 may be formed as a separate structure which may then be sewn, stitched, riveted or adhesively secured to the fabric surface area 90 of the garment 20 at about a distal end area 94 thereof.

As best seen in FIGS. 1-2, the tail 36 has a top diaper engaging surface area indicated generally at 36A and a bottom primary protective garment engaging surface area indicated generally at 36B. The top surface area 36A of the tail 36 is provided with a primary support coupler arrangement 52A, which is composed of a plurality of hooks arranged in a decorative design, such as the face of a puppy. The hooks of the coupler arrangement 52A are adapted to engage and securely grip a top fabric surface of the diaper 40, so the diaper 40 is secured to the protective garment 20 via the tail 36 of the support arrangement 30, with the tail 36 being held in its open position 60 (FIG. 2).

In a similar manner, the bottom surface area 36B of the tail 36 is provided with a secondary support coupler arrangement 52B, which is also provided with a plurality of hooks. The hooks of the secondary support coupler 52B are adapted to engage and securely grip the top fabric surface area 90 of the primary protection garment 20 for holding the tail 36 in a closed or support garment engaging position 62 (FIG. 1). The location of the garment support arrangement 30 is selected so that it may be easily and quickly utilized to grippingly hold or secure the diaper 40 in its intended and desired animal protective position at a rear bodily area 14 of the animal 12. This preferred position is also selected to be at a location where the support arrangement 30 can not be easily reached by the animal 12.

In summary then, a multi-functional animal protective garment 10 generally includes a primary protective garment 20 having an integral tail 36 moveable between an open secondary garment engaging position 60 and a closed primary garment engaging position 62. The tail 36 has a top surface area 36A and a bottom surface area 36B, where the top surface area 36A is provided with primary support coupler 52A for helping to fasten the tail 36 in its open position to a secondary animal protective garment 40 (a diaper or shield), and where the bottom surface area 36B is provided with secondary support coupler 52B for helping to fasten the tail 36 in its close position (a non diaper engaging position). In this manner, the tail 36 of the primary protective garment 20 is adapted to grip and hold the secondary animal protective garment 40 in its desired and intended animal protective position as best seen in FIG. 2.

Referring now to the drawings and more particularly to FIGS. 3-4, there is illustrated a self contained garment support kit 110, which kit 110 is also constructed in accordance with the present invention. The self contained garment support kit 110 may be easily and quickly attached to a primary animal protective garment 120, such as a protective animal vest, an animal sweater or animal T-shirt. When attached to the primary protective garment 120, the kit 110 provides the primary protective garment 120 with a completely new and unexpected secondary functions; namely, providing a storage area for a secondary animal protective garment, such as an animal diaper 40 and when needed a means of securing or supporting the diaper 40 in its intended and desired animal protective position when the diaper 40 has been secured to an animal 12.

The self contained garment support kit 110, when used in accordance with a novel method of using and attaching 1400 (FIG. 18) functions to provide the primary animal protective garment 120 with the capability of supporting an animal diaper 40 in its intended and desired animal protective position. The kit 110 in this regard, assures that the secondary animal protective garment or diaper 40 will not become dislodged due to normal animal activity movement, or because the diaper 40 becomes saturated with urine or the unwanted and undesired waste product of the animal 12.

In accordance with the novel method of using and attaching 1400, the garment support kit 110 in use provides several unique and unexpected advantages. More particularly, the support kit 110 may be easily and quickly secured to a primary animal protective garment 120 to provide the primary animal protective garment 120 with the above-mentioned secondary function. The kit 110 in this regard, when attached to the primary support garment 120, prevents a soiled or unsoiled animal diaper 40 from sliding off the animal 12 during normal animal activity movement and even when there is excessive diaper weight caused by the absorbent material of the diaper 40 becoming saturated with the waste product of the animal 12.

Another important advantage of the garment support kit 110 is that it can be easily and quickly coupled or attached to the secondary animal protective garment 120 in a very fast and convenient manner. Likewise, the kit 110 may be easily and quickly attached and detached from such a diaper 40, permitting the diaper 40 to be quickly and conveniently removed from the animal 12 so that the diaper 40 may be replaced if soiled or simply removed and temporarily set aside for later use, when the animal 12 is released to a suitable environment for waste elimination purposes.

Still yet another advantage of the garment support kit 110 is that it is universal in nature and may be utilized with different types and kinds of primary animal protective garments such as shirts, sweaters, and vests, to support various different types and kinds of diapers and shields. Another advantage provided by the garment support kit 110, is that the kit 110 is simplistic in nature, relatively inexpensive, and may be easily and quickly attached to a primary animal protective garment 120 for immediate use with another animal protective garment, such as a secondary animal protective garment 40, as best seen in FIG. 3. Finally, the garment support kit 110 may be provided in different sizes to accommodate different sized animals, such as teacup, miniature, small, medium, large and extra-large sized animals.

Considering now the garment support kit 110 in greater detail with reference to FIGS. 3-4, the garment support kit 110 generally comprises a garment support arrangement 130 which is provided with a base or pocket unit 132 having a closure flap 136. The garment support arrangement 130 is composed of a fabric material that is soft, pleasing to the touch, and decorative with an aesthetic appearance which may be selected to be coordinated in appearance to the primary animal protective garment 120. In this manner the garment support arrangement 130 maybe selected to enhance the overall decorative features of the primary animal protective garment 120 to provide a fashion statement.

The underside of the pocket unit 132 is provided with an adhesive backing 131 as best seen in FIG. 4, which enables the pocket unit 132 to be adhesively secured to a top fabric surface area 190 of the primary protective garment 120 at about or near a distal end portion thereof, as best seen in FIG. 3. The adhesive backing 131 is provided with a coating of a conventional fabric adhesive that functions to attach or secure the garment support arrangement 130 to the primary animal protective garment 120.

Although the attachment of garment support arrangement 130 to the primary support garment 120 has been described as an adhesive attachment, it is contemplated that other means of attachment could also be employed. For example, a set of hook or loop fasteners could be provided on the undersigned of the pocket unit 132 and a complimentary set of hook or loop fasteners could be adhesively secured to the fabric surface area 90 of the garment 120 so the hook and loop fasteners could be engaged to secure the support arrangement 130 to the garment 120. As another example, a set of fastening buttons and complementary button holes could be provided in the garment 120 so the arrangement 130 could be button fastened to the garment 120. Likewise a set of snap buttons could be attached to the garment 120 and to the underside of the pocket unit 132 to enable the arrangement 130 to be snapped placed on the garment 120. Based on the foregoing, there is no intention of limiting the manner in which the garment support arrangement 130 may be temporarily or removably secured to the garment 120 as other means of attachment are fully contemplated within the scope and spirit of the present invention. The important feature however, is that the arrangement 130 may be quickly attached or removed from the primary protective garment 120 for those times when the animal 12 needs or does not need to be protected with a diaper, such as the diaper 40. Moreover, the location of the garment support arrangement 130 is selected at about the distal end area of the primary protective garment 120 so that it may be easily and quickly utilized to grippingly hold or secure the diaper 40 in its intended and desired animal protective position at a rear bodily area 14 of the animal 12, while at the same time being positioned at a location where it can not be easily reached by the animal 12.

Considering now the closure flap 136 in greater detail, with respect to FIGS. 3-4, the closure flap 136 is stitched to the pocket unit 132 at about a tail facing end or distal boundary end of the pocket unit 132 indicated generally at 194. In this regard, the closure flap 136 is moveable or foldable about the distal end 194 of the pocket 132 from a closed or pocket sealing position 62 as best seen in FIG. 4 to an open or diaper engaging position 60 as best seen in FIG. 3. In this regard, the closure flap 136 has a sufficient length dimension and a sufficient width dimension to overlay a substantial top surface proximal end area of the diaper 40 when the flap 136 is disposed in the open or diaper engaging position 60 as best seen in FIG. 3.

The closure flap 136 has a top diaper engaging surface area indicated generally at 136A (FIG. 4) and a bottom base unit engaging surface area indicated generally at 136B (FIG. 3). The top surface area 136A of the closure flap 136 is provided with a primary support coupler 152A, which is composed of a plurality of hooks arranged in a decorative design as best seen in FIG. 4. The hooks of the primary support coupler 152A are adapted to engage and securely grip a top fabric surface of the diaper 40 so the diaper 40 and the closure flap 136 are coupled removably together so the diaper 40 may not be dislodged from the animal 12.

In a similar manner, the bottom surface area 136B is provided with a secondary support coupler 152B, which is also provided with a plurality of hooks that are adapted to engage and securely grip a pocket fasteners 133 which is secured to a top surface floor area 138 of the pocket unit 132. In this regard, the pocket fastener 133 is composed of a plurality of loops which will engage the hooks of the secondary support coupler 152B to grip or fasten the closure flap 136 in its closed position 62. As best seen in FIG. 3, the secondary support coupler 152B and the pocket fasteners 133 are arranged in a raised U-shaped configuration so as to provide a standoff from the floor or inner face 136B of the closure flap 136 and a corresponding standoff from the floor area 138 of the pocket unit 132. This is an important feature of the present invention, as in combination when the pocket fasteners 133 and secondary support coupler 152B are fastened together they form a pocket space with a sufficient height, width and depth dimension for receiving therein a folded, packaged diaper, that can be retrieved and utilized on the animal 12 when needed. In this regard, the fabric construction of the pocket unit 132 allows it to be easily conformed about the packaged diaper so the diaper 40 is secured within the pocket unit 132 for future use when needed.

By way of example only, and without intending any limitation on the size or appearance of the primary support coupler 152A, it may be of different sizes and configurations. For example, it may be in the configuration of the face of an animal, such as the face of a dog as best seen in FIG. 4, or it may have a pattern or shape that complements the pattern of the fabric forming the primary protective garment 120. The primary support coupler 152A does have however, a sufficient diaper engaging surface area so that a set of hooks formed into the above-mentioned pattern or shape will engage and grip the outer material surface of the diaper 40. In this regard, most if not all diapers are composed of an open weave fabric with a plurality of fiber like loops. These loops when engaged with the hooks of the support coupler 152A become intertwined with the hooks to form a plurality of small fasteners deployed across the outer surface area of the support coupler 152A. This engagement of hooks and loops is sufficient to prevent the diaper 40 from freeing itself from the primary support coupler 152A and its associated carrying member, the closure flap 136.

Figure 16:
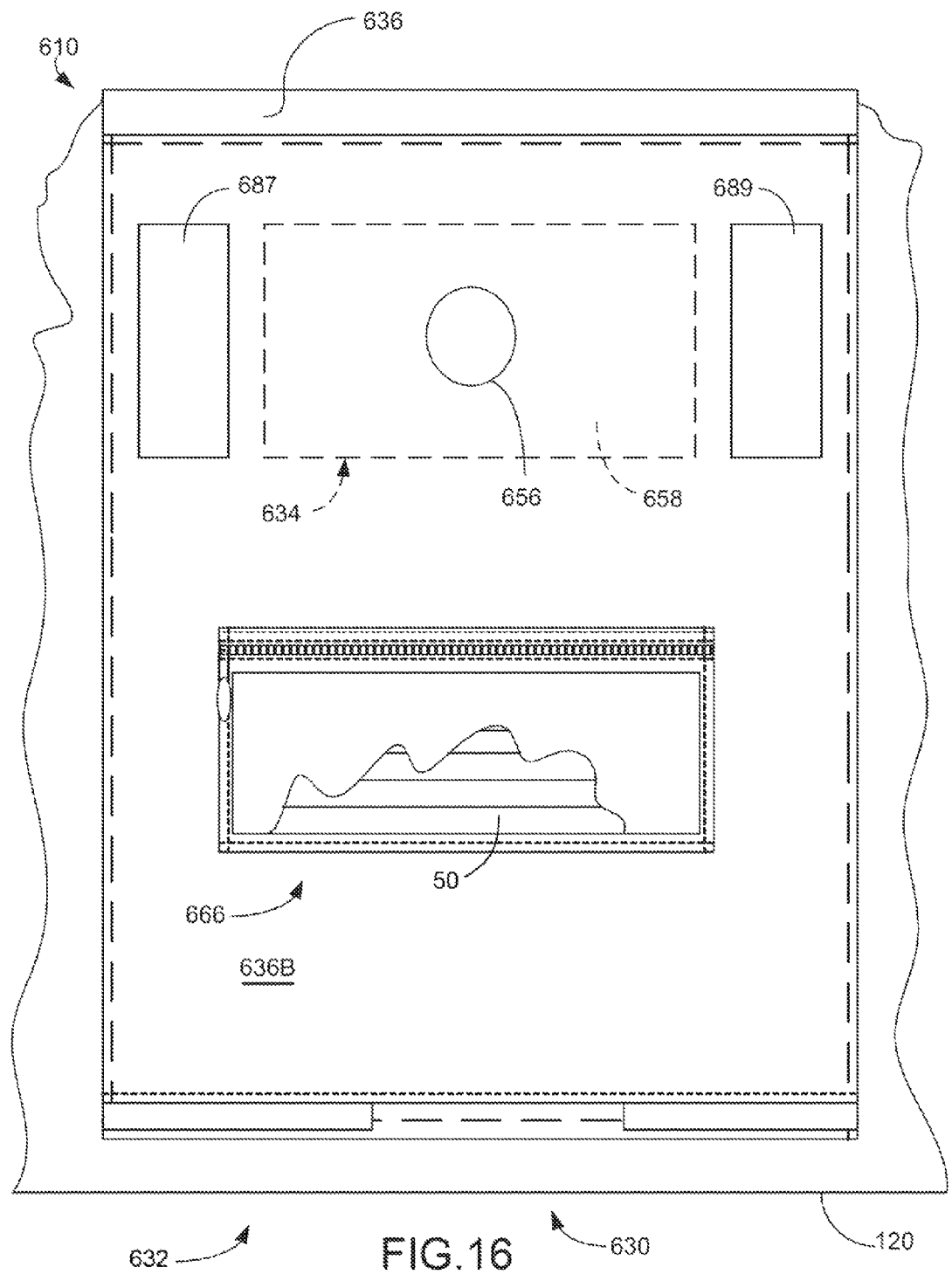
FIG. 16 is a top plane view of yet another self contained diaper support garment, which is constructed in accordance with the present invention.
Figure 17:
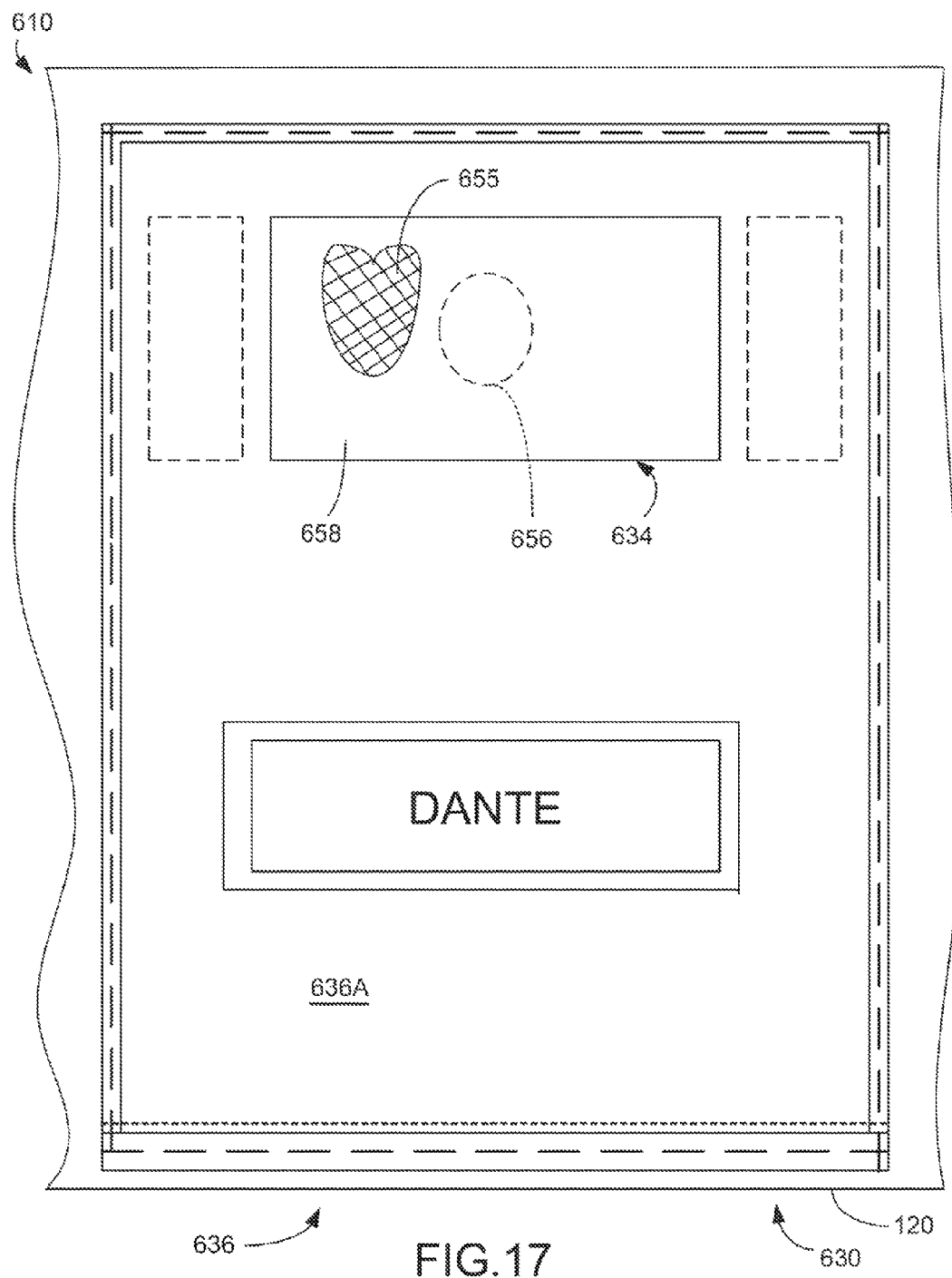
FIG. 17 is a top plane view of another diaper support garment, which is constructed in accordance with the present invention.

Considering the primary coupler 152A in still greater detail, the primary support coupler 152A in one preferred embodiment is sewn to the outside or diaper engaging surface area 136A of the closure flap 136. There is no intention however, of limiting the manner of attaching the primary support coupler 152A to the closure flap 136 by this method. Other methods of attachment are contemplated and will be described hereinafter in greater detail. For example in other preferred embodiments of the present invention as best seen in FIGS. 16-17, a primary support coupler 634, rather than being permanently secured to a closure flap 636 may be removable secured to the closure flap 636. In this regard, the primary support coupler is a removable stick pin device 634 having a male pin component, such as a male pin component 656 (FIG. 16) and a female securing component 658 (FIG. 17) which receives the male pin component 656 in a friction-tight fit. The female securing component 658 is provided with a set of hook or loop fasteners configured in a decorative design 655, such as the face of a dog, the face of a cat, a Christmas tree, a flag, or emblem design for example. With this arrangement, when the closure flap 636 is disposed in its closed position 62, the decorative design of the female securing component 658 is clearly seen and complements the decorative design of the primary animal protective garment 120.

When the closure flap 636 is moved to the open or deploying position 60 the back side or un-decorative side of the male pin component 656 is seen, while the female fastening elements in the form of the set of hook or loop fasteners is brought into engagement with the material or fabric surface of the diaper 40. From the forgoing, it is clear that the primary support coupler 634 when not in use securing the diaper 40 to the primary animal protective garment 120 has a secondary function, namely that of supplementing the decorative design provided by the primary animal protective garment 120.

As will be explained hereinafter in greater detail, the male pin component 656 (FIGS. 16-17) may be separated from the female fastening component 658 and substitute female fastening components may be utilized to provide the closure flap 636 with different types of decorative designs, which may be desired because of the seasons and special holidays. It is also possible to reverse the female fastening component so that it is disposed on the concealed side of the closure flap 636. This reversal is used for those situations where the garment support arrangement 630, is carried on an inner or inside fabric surface area of the primary animal protective garment 120. This embodiment of the present invention is for those situations where the overall length of the primary animal protective garment 120 is structure so as to overlay the diaper 40. When this occurs, the closure flap 636 is moved to its open position 60 to permit the female fastening component 658 to engage the fabric surface of the diaper 40. In this configuration, the distal end area of the protective garment 120 may be folded over a sufficient distance to expose the garment support arrangement 630 so that it is not in direct contact with the body of the animal until such time as a diaper 40 is placed on the animal. This configuration simply addresses where the overall length of the primary animal protective garment 120 is such that it overlays the diaper 40 as opposed to being spaced from the diaper 40 as best seen in FIG. 3 which would be considered the more normal situation.

From the foregoing, those skilled in the art will appreciate that the closure flap 636 may be provided with a removable or interchangeable primary support coupler, or it may be provided with a permanent set of hook or loop fasteners secured to either the exposed or concealed surfaces of the closure flap 136. In these configurations, the hook or loop fasteners may also be provided in a decorative pattern to complement the fabric design features of the primary animal protective garment 120. There is therefore no intention of limiting the disclosed invention to that of a removable or interchangeable primary support coupler 634 or a permanently attached support coupler 152A as described herein.

Referring now to the drawings and more particularly to FIGS. 5-6, another self contained garment support kit 210 constructed in accordance with another exemplary embodiment of the present invention is illustrated. The garment support kit 210, like garment support kit 110 is adapted to be removably secured to a primary animal protective garment 120 in the same manner as described relative to the garment support kit 110 and therefore the manner in which the kit 210 is secured to the primary animal protective garment 120 will not be described hereinafter in greater detail.

The self contained garment support kit 210 may be easily and quickly attached to a primary animal protective garment 120, such as a protective animal vest, animal sweater or animal shirt. When so attached, the kit 210 provides the primary protective garment 120 with a completely new and unexpected secondary functions; namely, 1) a storage area for a diaper 40; and 2) when needed, means for securing or supporting the secondary animal protective garment 40 in its intended and desired animal protective position.

The self contained garment support kit 210, when used in accordance with a novel method of using and attaching 1400 (FIG. 18) functions to provide the primary animal protective garment 120 with the capability of supporting an animal diaper 40 in its intended and desired animal protective position. The kit 210 in this regard, assures that the secondary animal protective garment or diaper 40 will not become dislodged due to normal animal activity movement, or because the diaper 40 becomes saturated with urine or the unwanted and undesired waste product of the animal 12. The garment support kit 210, like garment support kit 110 is adapted to be removably secured to a primary animal protective garment 120 in the same manner as described relative to the garment support kit 110 and therefore the manner in which the kit 210 is secured to the primary animal protective garment 120 will not be described hereinafter in greater detail.

Considering now the garment support kit 210 in greater detail with reference to FIGS. 5-6, the garment support kit 210 generally includes a garment support arrangement 230 which is provided with a base or pocket unit 232 having a diaper engaging closure flap 236 and a coupler engaging closure flap 237. The diaper engaging closure flap 236, like closure flap 136 is adapted to carry a primary support coupler 234 into position for grippingly engaging the secondary animal protective garment, such as a diaper 40. The coupler engaging closure flap 237 on the other hand, is adapted to carry a storage compartment indicated generally at 240. As a secondary function, the closure flap 237 is further adapted to help secure tethered secondary support couplers, such as a support coupler 250, to a floor area 242 of the pocket unit 232 when such secondary support couplers 250 are deployed for helping to support the diaper 40 as will be explained hereinafter in greater detail.

Considering now the secondary support couplers 250 in greater detail with reference to FIGS. 5-6, unlike garment support kit 110, the garment support kit 210 is provided a plurality of support couplers of different types and kinds for engaging and supporting the diaper 40 in its desired and intended animal protective position. The reason for providing a plurality of support couplers of different types and kinds is to facilitate the absolute securing of the diaper 40 to the garment support arrangement 230 regardless of the construction of the diaper 40. For example, a diaper may be constructed of an outer plastic material with a fabric-like, highly absorbing inner material, where the outer plastic material would not have a sufficient open weave of loops that could engage the hooks otherwise provided on primary coupler 234. Accordingly, different types and kinds of couplers, such as the secondary coupler 250 are provided with the garment support kit 210 to accommodate such different diaper constructions.

In view of the above-described need, the closure flap 237 has a dual purpose as mentioned earlier: first, it provides a storage space or storage compartment 240 for storing a packaged diaper (not shown) and one or more secondary couplers, such as the secondary coupler 250. Secondly, it is for supporting in a diaper engaging position, one or more of deployed secondary couplers, such as the secondary coupler 250, when such a secondary coupler 250 is utilized to further secure the diaper 40 in its intended and desired animal protective position as best seen in FIG. 6. The manner in which a secondary coupler is deployed and utilized to secure the diaper 40 will be described hereinafter in greater detail.

Like the garment support arrangement 130, the garment support arrangement 230 is also composed of a fabric material that is soft and pleasing to the touch, and decorative with an aesthetic appearance which may be selected to be coordinated in appearance to the primary animal protective garment 120. In this manner the garment support arrangement 230 maybe selected to enhance the overall decorative features of the primary animal protective garment 120 to provide a fashion statement.

Considering now the closure flap 236 in greater detail, with respect to FIGS. 5-6, the closure flap 236 is stitched to the pocket unit 232 at about a tail facing end or distal boundary end of the pocket 232 indicated generally at 294. In this regard, the closure flap 236 is moveable or foldable about and away from a distal end area 294 of the pocket 232 from a closed or pocket sealing position, such as similar to that closed position 62 of the closure flap 136 as best seen in FIG. 4, to an open position 60 as best seen in FIGS. 5-6. In this regard, the closure flap 236 has a sufficient length dimension and a sufficient width dimension to overlay a substantial top surface proximal end area of the diaper 40 when the flap 236 is disposed in the open or diaper engaging position 60 as best seen in FIG. 6.

The closure flap 236 has a top or diaper engaging surface area indicated generally at 236A and a bottom or a base unit engaging surface area indicated generally at 236B. The top surface area 236A of the closure flap 236 is provided with the primary support coupler 234, which is substantially similar to primary support coupler 234 and will not be described hereinafter in greater detail except to mention that the primary support coupler 234 is adapted to engage and securely grip a top fabric surface of the diaper 40 so the closure flap 236 is held in its open position 60 (FIG. 6) in a tight gripping relationship with the diaper 40. In this manner the diaper 40 is removably secured to the closure flap 236 via the primary support coupler 234.

As mentioned earlier, whenever the open weave or loop-like construction of the diaper 40 is not sufficiently open to provide an absolute gripping relationship with the hooks of the primary coupler 234, the gripping function of the primary coupler 234 may be reinforced, supplemented or completely substituted with one or more secondary couplers 250 as best seen in FIG. 5-6. When such additional or substitute support is required, the closure flap 237 may be moved from its closed position as best seen in FIG. 6, to its open position as best seen in FIG. 5 which exposes the storage compartment 240. When so exposed, a user may easily retrieve at least one secondary support coupler 250 from the storage compartment 240 for use.

As best seen in FIG. 5, when the closure flap 237 is moved to its open position, toward the proximal end of the primary protective garment 120, the floor area 242 of pocket 232 is also exposed. The floor area 242 is provided with a set of tether pins, such as a male tether pin 252 which is adapted to receive and secure a proximal end of a secondary coupler 250 so the proximal end of the coupler 250 may be tethered at this pin point and deployed. In this regard, the proximal end of the coupler 250 is provided with a female pin receiving component 253 that snaps onto the tether pin 252 for securing the coupler 250 to the floor 242 of the pocket 232. Once, one or more of the secondary couplers are deployed, the closure flap 237 may then be returned to its closed position (FIG. 6) where fasteners 238 and 239 engage one another to hold the flap 237 in its closed position. In this closed position, flap 237 overlays the couplers 250 helping to secure them within the pocket unit 232. The secondary coupler 250, which is provided with diaper attachments means, such as a clam shaped clip 254 which may then be attached to the diaper 40 to supplement the securing role of the primary coupler 234.

In those situations where the primary coupler 234 is unable to grip the weave of the diaper 40 or in those situations where the gripping force of the primary coupler 234 is so sufficiently weak that it may be easily disengaged from the diaper 40, the closure flap 236 being moved to a closed position, similar to the closed position illustrated in FIG. 7, where the closure flap 236 overlays closure flap 237. A closure flap fastener 235 disposed on the closure flap 236 may then engage and grip another closure fastener 233 disposed on an upper surface area 237A of the closure flap 237 to secure the closure flap 236 in its closed position. In this manner, the closure flap 236 in its closed position further facilitates securing the secondary couplers, such as the couplers 250 within the pocket unit 232.

Again referring to FIG. 5, the secondary storage compartment indicated generally at 240 has a sufficient volume for the storage of a packaged diaper and at least two secondary support couplers, such as the support coupler 250. It is contemplated that different types and kinds of secondary support couplers may be provided with the garment support kit 210, including but not limited to, fixed length support couplers, variable length support couplers, elastic support couplers, clam shell support couplers, alligator clip support couplers, draw string support couplers, and hook and loop support couplers. Most, if not all of these different types and kinds of support couplers will be described hereinafter in greater detail.

Referring now to the drawings and more particularly to FIGS. 7-8, a multi-purpose pet protection garment according to another exemplary embodiment of the present invention is illustrated and is shown generally at reference character 310. The pet protection garment 310, when used in accordance with a novel method of use 1400 (FIG. 8), functions to grip and securely hold a secondary animal protective garment, such as a diaper or shield 40, in its intended and desired animal protective position, even though the diaper 40 may be fully loaded or completely saturated with animal waste product. The protection garment 310 also sufficiently grips and holds the diaper 40 when it is being worn by an older animal whose back may be so severely slanted that it would be difficult, if not impossible, to otherwise securely hold the diaper 40 in its intended and desired animal protective position due to undesired and unwanted unloaded diaper slippage.

The pet protection garment 310, generally comprises: (1) a primary animal protective garment 120, such as a protective animal vest, a pressure wrap garment, a T-shirt, or a sweater, and (2) a garment support arrangement 330, which is either integral to or sewn (attached) onto and carried by the primary animal protective garment 120. The primary pet protection garment 120 may be worn by a dog or cat or nearly any other type of animal with a similar body construction to that of a dog or cat. The primary animal protective garment 120 functions to protect the animal 12 from environmental conditions or it may be configured with simple or complex fabric design features so that it further functions as a decorative fashion wear item or a fashion statement item worn by the animal 12. More particularly, the primary animal protective garment 120 may comprise a water-repellant fabric to protect the animal from raining weather, a thick quilted fabric to protect the animal from cold weather or a light-weight print fabric arranged in a highly decorative pattern. Other fabric structures and primary animal protective garment purposes are clearly contemplated relative to the present invention, so there is no intention of limiting the fabrics or the purpose of the primary protective garment to those mentioned herein.

Considering now the garment support arrangement 330 in greater detail with reference to FIGS. 7-8 the garment support arrangement 330 is provided with a pocket area indicated generally at 332 with a closure flap 336 having an inside surface area 336B and an outside surface area 336A. The garment support arrangement 330 is permanently secured to the animal protective garment 120 substantially as in the manner as the garment support arrangement 30 was secured to the protective garment 10. Similarly, the garment support arrangement 330 is substantially similar in construction to the garment support arrangement 230 except that the arrangement 330 is permanently attached to the protective garment 120 as opposed to be removably attached as was the case of the garment support arrangement 230. A fastener 335 on an inside surface area 336 of the closure flap 336, similar to fastener 235 cooperates with a pocket fastener 333, similar to fastener 233, to hold the closure flap 336 in its closed position as best seen in FIG. 7. One other difference regarding the garment support arrangement 330 is that it is not provided with a coupler engaging closure flap, such as the closure flap 237 as previously described. In the absence of the closure flap 237, the secondary support couplers are stored in the pocket 332 area and are tethered by tether pins 352 extending upwardly from a floor area 342 of the pocket 332. It is anticipated that this embodiment would be employed when the user is aware that the utilized diaper 40 does not have a strong open weave, and therefore the utilization of the secondary couplers, such as a secondary coupler 250 will be anticipated in most situations. Because of these similarities, the garment support arrangement 330 will not be described hereinafter in greater detail except for the discussion that follows relative to the different types and kinds of secondary support couplers.

Figure 13:
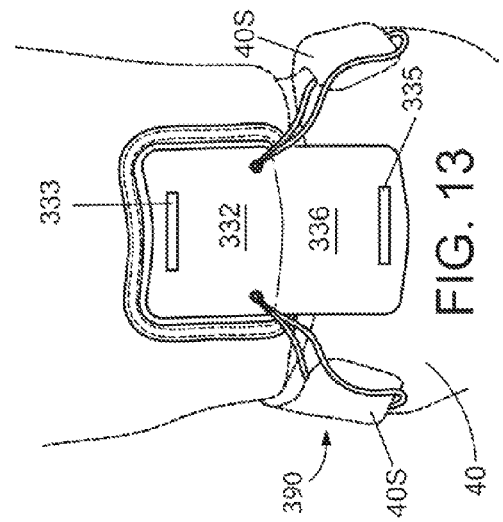
FIG. 13 is a top plane view of the diaper support garment of FIG. 9, illustrating its primary support coupler and its secondary support coupler both engaging and supporting an animal diaper, where the secondary support coupler is an elastic loop coupler.
Figure 10:
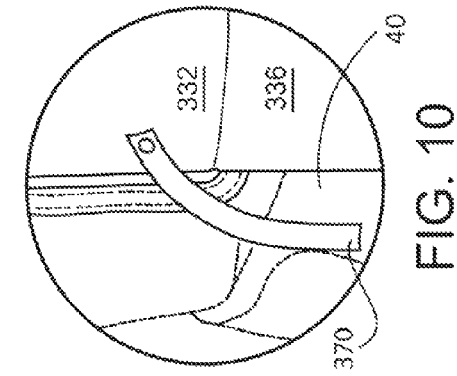
FIG. 10 is a top plane view of the diaper support garment of FIG. 9, illustrating its primary support coupler and its secondary support coupler both engaging and supporting an animal diaper, where the secondary support coupler is an elastic band coupler having a plurality of hooks.
Figure 11:
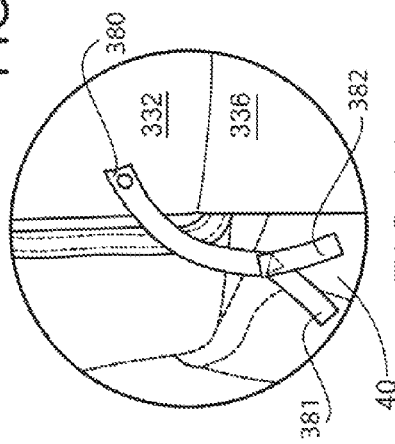
FIG. 11 is a top plane view of the diaper support garment of FIG. 9, illustrating its primary support coupler and its secondary support coupler both engaging and supporting an animal diaper, where the secondary support coupler is a split elastic band coupler having a plurality of hooks.
Figure 9:
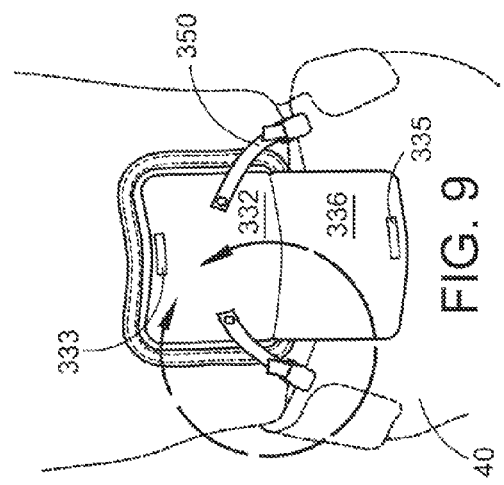
FIG. 9 is a top plane view of yet another diaper support garment having a single compartment construction and a plurality of support couplers, including a single primary support coupler and a plurality of secondary support couplers, which garment is constructed in accordance with the present invention.
Figure 12:
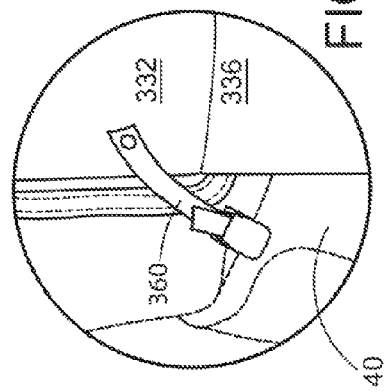
FIG. 12 is a top plane view of the diaper support garment of FIG. 9, illustrating its primary support coupler and its secondary support coupler both engaging and supporting an animal diaper, where the secondary support coupler is a clip supported by an adjustable length strap.

Considering now the different types and kinds of secondary support couplers that may be deployed for supplemental support of the diaper 40, reference may be made to FIGS. 9-13, where FIG. 9 is substantially similar to FIG. 8 which illustrates the closure flap 336 in an open diaper engaging position. The only difference between FIG. 8 and FIG. 9 in this case is with reference to the secondary support couplers. In this regard, the secondary support coupler 250 as best seen in FIG. 7-8 is a fixed length support coupler, whereas the secondary support coupler 350 as best seen in FIG. 9 is an adjustable length coupler. Similar differences are disclosed relative to FIGS. 10-13, where FIG. 10 illustrates an elastic band type secondary coupler 370 with a set of hooks that may be utilized to fasten to the diaper 40. FIG. 11 illustrates an elastic Y-band type secondary coupler 380 with extension arms 381 and 382 respectively, each having a set of hooks to allow one arm to extend over the outer surface area of the diaper 40 and the other arm, if desired to extend over the inner surface area of the diaper 40 in a pinching configuration. For clarity of illustration the two arms 381, 382 in FIG. 11 are both shown engaging the outer surface area of the diaper 40. FIG. 12 is substantially similar to FIG. 9 except the strap of the secondary coupler in this embodiment is an adjustable elastic strap coupler 360 as opposed to an adjustable fixed length strap coupler 350 as illustrated in FIG. 9, FIG. 13 illustrates an elastic loop secondary coupler 390, where the loop is utilized in combination with the normal diaper securing straps 40S; e.g. the loops support the straps 40S to hold them securely to the garment support arrangement.

Referring now to the drawings and more particularly to FIG. 14, another multi-purpose pet protection garment 410 is illustrated, which pet protection garment 410 is constructed in accordance with another exemplary embodiment of the present invention is illustrated. The pet protection garment 410, when used in accordance with a novel method of use 1400 (FIG. 18), functions to grip and securely hold a secondary animal protective garment, such as a diaper or shield 40, in its intended and desired animal protective position, even though the diaper 40 may be fully loaded or completely saturated with animal waste product. The protection garment 410 also sufficiently grips and holds the diaper 40 when it is being worn by an older animal whose back may be so severely slanted that it would be difficult, if not impossible, to otherwise securely hold the diaper 40 in its intended and desired animal protective position due to undesired and unwanted unloaded diaper slippage.

As best seen in FIG. 14, the pet protection garment 410 generally comprises: (1) a primary animal protective garment 120, such as a protective animal vest, a pressure wrap garment, a T-shirt, or a sweater, and (2) a garment support arrangement 430, which is integral to or attached and carried by the primary animal protective garment 120. The garment support arrangement 430 generally includes a base or pocket unit 432 that is secured to the primary animal protective garment 120 at about its distal end. The preferred method of attachment is by stitching the support arrangement 430 to the underlying garment 120, but as mentioned earlier other means of attachment are fully contemplated by the present invention. Attached to the base pocket unit 432 at about its distal end boundary is a closure flap 436 having an outside surface area 436A and an inside surface area 436B, which closure flap 436 is moveable between a closed position and an open position in the same manner as closure flap 36.

Considering now the utility pocket 432 in greater detail with reference to FIG. 14, the utility pocket 432 is provided with a zipper pocket assembly 466, a pair of tether pads indicated generally at 444 and fasteners indicated generally at 433. As will be explained hereinafter in greater detail, each tether pad 444 is provided with a detent indicated generally at 442 which is adapted to secure and retain on the pad 444, a secondary support coupler, such as a secondary support coupler 450. The distal end of the support coupler 450 is provided with an eyelet that engages and slides the detent 442 inwardly when the eyelet is pressed down onto the pad 444 and once the eyelet passes the detent 442 the detent 442 slides back to its extended position substantially preventing the eyelet of the coupler from escaping from the pad 444.

Considering now the zipper pocket assembly 466 in greater detail, the zipper pocket assembly 466 generally comprises overlaying inside and outside pocket layers 481, 482, which are joined together along peripheral edges indicated at stitching lines 483, 484, and 485 respectively. When so stitched together, the utility pocket 432 is then provided with a secondary support coupler storage compartment, indicated generally at 438. The storage compartment 438 has an access opening 486 with a zipper closure 488. The storage compartment 438 has a sufficient storage capacity for receiving and storing therein a packaged diaper (not shown) and at least two support couplers, such as the support coupler 450. With this arrangement, access to the zipper pocket assembly 466 and the support couplers stored therein is prevented, when the closure flap 436 is disposed in its close position.

As noted herein earlier, the garment support arrangement 430 is disposed at a distal end area of the primary protective garment 120 so that when the closure flap 436 is moved to its open position, the primary support coupler (not shown) carried by the closure flap 436 is deployed for engagement with the diaper 40. When the flap 436 is so positioned in its open position, the spacing difference between the primary protective garment 120 and the diaper 40 should be sufficiently small so the closure flap 436 will be deployed in an overlaying relationship with the diaper 40. In this manner then, the primary support coupler is positioned to be easily positioned by the user gripping the flap 436 and then fastened to the secondary protective garment or diaper 40 so the diaper 40 is securely held in its intended and desired animal protective position. While deployment of the primary support coupler as described above is generally successful, the utilization of a secondary support coupler 450 may be needed, when (1) the spacing difference between the primary protective garment 120 and the diaper 40 is so great that the closure flap 436 when moved from its close position to its open deployment position to deploy the primary support coupler, does not result in an overlaying relationship. When this occurs, the utilization of a secondary support coupler, such as the secondary support coupler 450 may be required.

Figure 15:
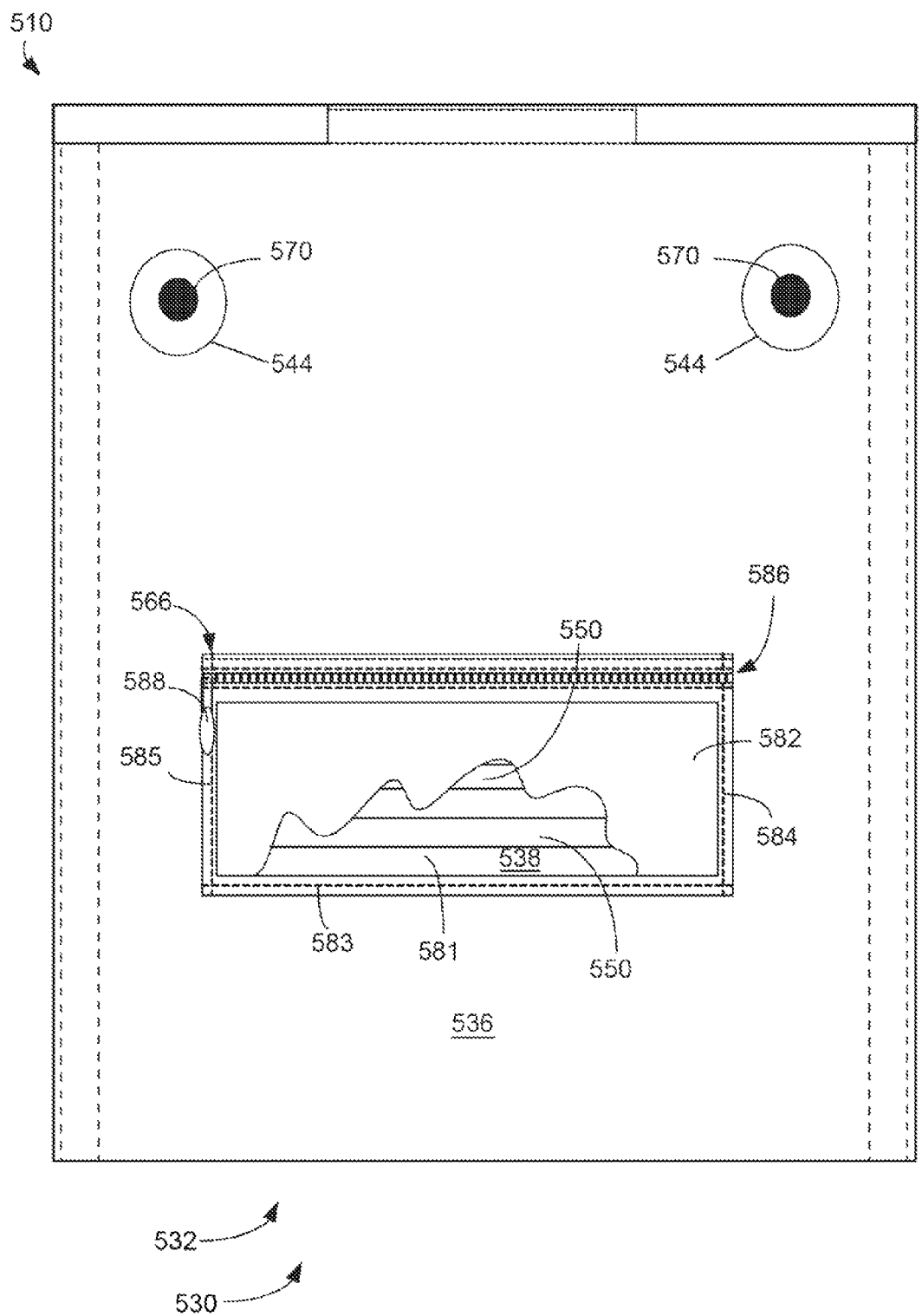
FIG. 15 is a top plane view of still yet another diaper support garment, which is constructed in accordance with the present invention.

As best seen in FIG. 15, it is contemplated that in yet another preferred embodiment a pet protection garment 510, with either an integral or separately attached and permanently secured garment support arrangement 530. The garment support arrangement 530 is provided with a pocket area 532 with a closure flap 536. The support arrangement 530 in this embodiment is provided with a different construction. That is, rather than the zipper pocket assembly and tether pin pads being disposed in the pocket area of the support arrangement 530, they are disposed on the closure flap 536. In this regard, the garment support arrangement 530 is provided with a base or utility pocket 532 and a closure flap 536 each provided with a fastener, such as previously described that permits the closure flap 536 to seal and close the pocket 532. The closure flap 536 in this arrangement is provided with a zipper pocket assembly 566, and a pair of tether pads indicated generally at 544. Each tether pad 544 is provided with a female snap pin receptacle 570 that will receive a corresponding male snap pin (not shown) disposed on the distal end of a secondary support coupler 550. In this configuration the zipper pocket assembly 566 generally comprises overlaying inside and outside pocket layers 581 and 582 which are joined together along peripheral edges indicated at stitching lines 583, 584, and 585. When so stitched together, the closure flap 536 is then provided with a backup storage compartment, indicated generally at 538. The storage compartment 538 has an access opening 586 with a zipper closure 588. The storage compartment 538 has a sufficient storage capacity for receiving and storing therein a package diaper (not shown) and at least two support couplers, such as the support coupler 550. With this arrangement, access to the storage compartment 538 and the support couplers stored therein is prevented when the closure flap 536 is disposed in its close position.

Referring now to the drawings and more particularly to FIGS. 16-17, a multi-purpose pet protection garment according to another exemplary embodiment of the present invention is illustrated and shown generally at reference character 610. The pet protection garment 610 when used in accordance with a novel method of use 1400 (FIG. 18), functions to grip and securely hold a secondary animal protective garment, such as a diaper or shield 40, in its intended and desired animal protective position, even though the diaper 40 may be fully loaded or completely saturated with animal waste product. The protection garment 610 also sufficiently grips and holds the diaper 40 when it is being worn by an older animal whose back may be so severely slanted that it would be difficult, if not impossible, to otherwise securely hold the diaper 40 in its intended and desired animal protective position due to undesired and unwanted unloaded diaper slippage.

The pet protection garment 610 generally comprises: (1) a primary animal protective garment 120, such as a protective animal vest, a pressure wrap garment, a T-shirt, or a sweater, and (2) a garment support arrangement 630, which is carried by the primary animal protective garment 120. The garment support arrangement 630 generally includes a base utility pocket unit 632 that is secured to the primary animal protective garment 120 at about its distal end. The preferred method of attachment is by stitching the support arrangement 630 to the underlying garment 120, but as mentioned earlier other means of attachment are fully contemplated by the present invention. Attached to the base pocket unit 632 at about its distal end boundary is a closure flap 636 which is moveable between a closed position and an open position in the same manner as closure flap 336.

Considering now the closure flap 636 in greater detail, the closure flap 636 has a diaper engaging surface 636A and a pocket engaging surface area 636B. Disposed on the diaper engaging surface 636A is a primary coupler 634 (FIG. 17). Disposed on the pocket engaging surface area 636B is a zipper pocket assembly 666 (FIG. 16) and a pair of tether pads indicated generally at 687 and 689 respectively. As will be explained hereinafter in greater detail, each of the tether pads 687,689 are adapted to receive thereon and secure thereto a secondary support coupler, such as a secondary support coupler 50.

Referring now to the drawings and more particularly to FIGS. 19-22 another multi-purpose pet protection garment 1310 is illustrated, which garment 1310 is also constructed in accordance with the present invention is illustrated. The pet protection garment 1310, when used in accordance with a novel method of use 1400 (FIG. 18), functions to grip and securely hold a secondary animal protective garment, such as a diaper or shield 40, in its intended and desired animal protective position, even though the diaper 40 may be fully loaded or completely saturated with animal waste product. The protection garment 1310 also sufficiently grips and holds the diaper 40 when it is being worn by an older animal whose back may be so severely slanted that it would be difficult, if not impossible, to otherwise securely hold the diaper 40 in its intended and desired animal protective position due to undesired and unwanted unloaded diaper slippage.

Figure 19:
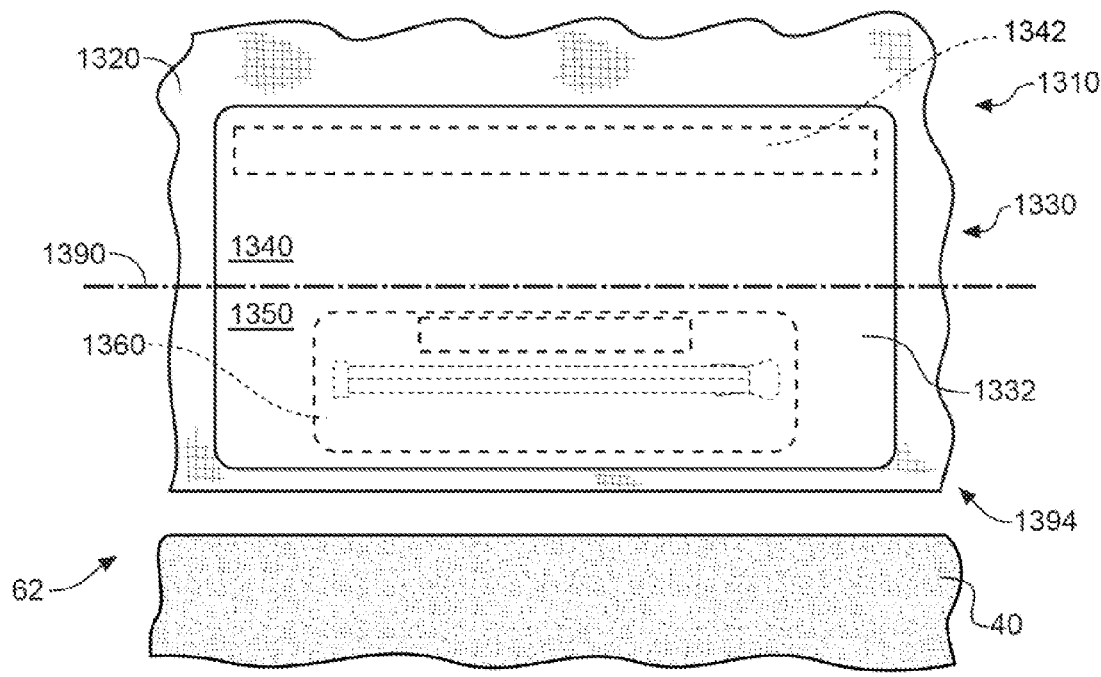
FIG. 19 is top plane view of yet another diaper support kit which is constructed according to the present invention illustrating the support kit being worn in combination with a dog diaper.
Figure 20:
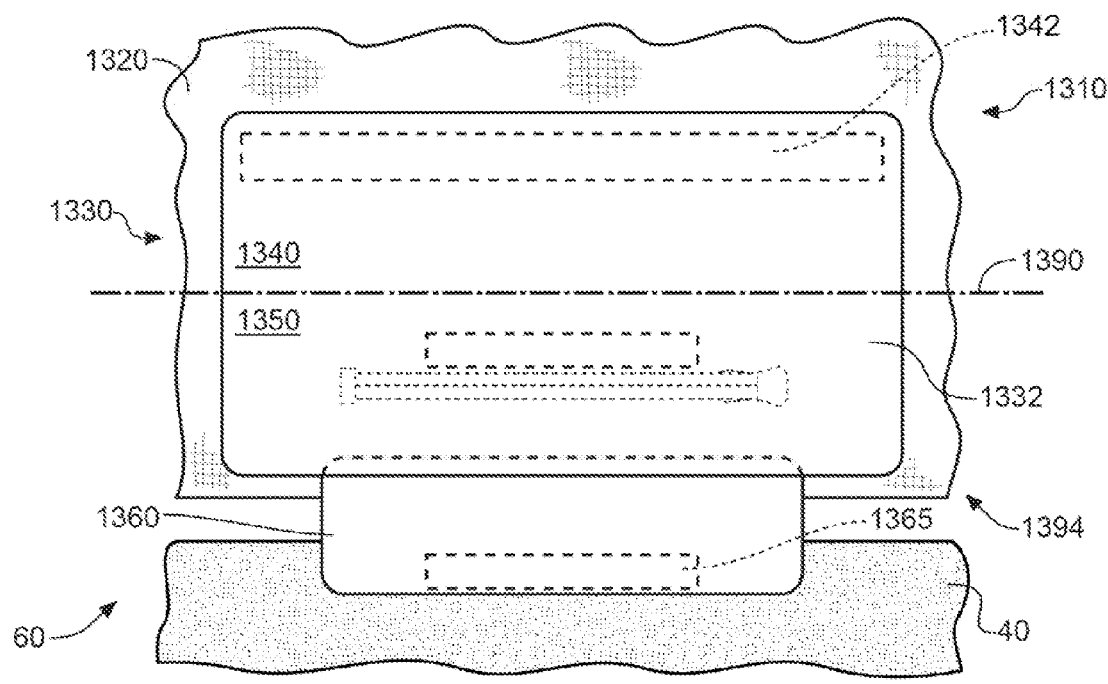
FIG. 20 is a top plane view of the diaper support kit of FIG. 19, illustrating its integrally formed support coupled extended into a diaper support position for supporting a associated dog diaper.
Figure 21:
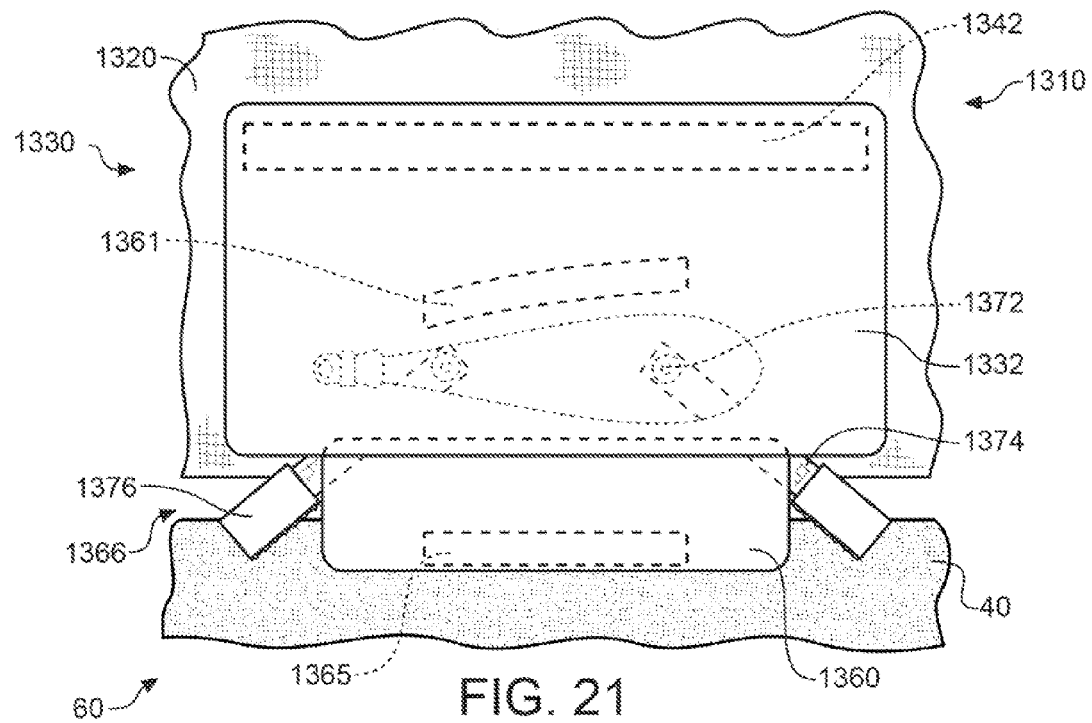
FIG. 21 is a top plane view of the diaper support kit of FIG. 19, illustrating its secondary support couplers cooperating with its integrally formed support coupler for supporting a dog diaper.

As best seen in FIGS. 19-22, the pet protection garment 1310 generally comprises: (1) a primary animal protective garment 1320, such as a protective animal vest, a pressure wrap garment, a T-shirt, or a sweater, and (2) a garment support arrangement 1330, which is carried by the primary animal protective garment 1320. The garment support arrangement 1330 generally includes a base unit 1332 having an upper section 1340 and a lower section 1350. A protective flap or tail 1360 is secured to the base unit 1332 which functions to carry a primary diaper coupler 1365. The protective flap or tail 1360 is secured along its distal end as best seen in FIG. 20, to a distal end area of the base unit 1332 to facilitate its rearward extension from the base unit 1332 a sufficient distance so that the flap 1360 overlays a substantial top surface proximal end area of the diaper 40 when the flap or tail 1360 is disposed in an open or diaper engaging position, indicated generally at 60, as best seen in FIGS. 20-21.

The upper and lower sections 1340 and 1350 respectively, are integrally attached to one another along an imaginary lateral line indicated generally at 1390 as best seen in FIG. 19; and although the upper section 1340 is permanently secured by its proximal boundary end area to the animal protective garment 1320 by attachment means indicated generally at 1342, the lower section 1350 is not. In this regard, the lower section 1350 is not secured to the animal protective garment 1320 so that it may be lifted up and away from the protective garment 1320 and folded back onto or rotated forwardly onto overlaying the upper section 1340.

The lower section 1350 when folded back onto the upper section 1340 exposes the tail 1360 so that it may be gripped and pulled forward toward the rear or tail end of an animal 12 a sufficient distance so that the tail 1360 overlays a substantial top surface area of the diaper 40. In this manner, a primary diaper coupler 1365 carried by the tail 1360 may be brought into gripping, securing engagement with the top fabric surface area of the diaper 40 for holding or securing the diaper 40 in its intended animal protection position as best seen in FIGS. 20-21.

Figure 22:
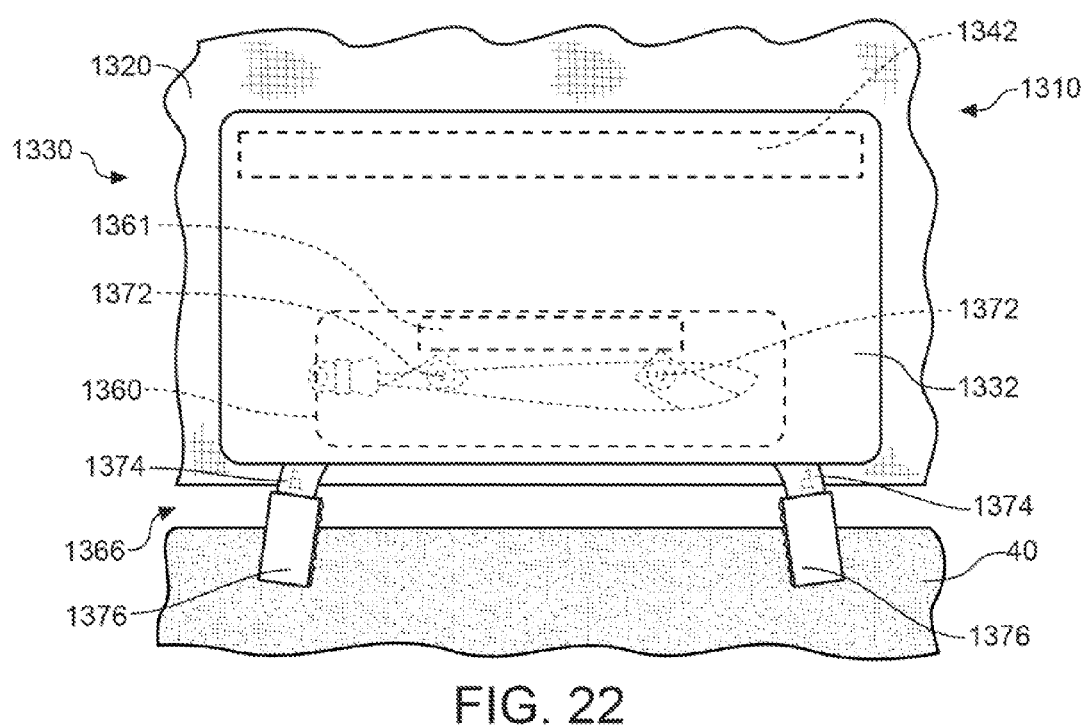
FIG. 22 is a top plane view of the diaper support kit of FIG. 19, illustrating its secondary support couplers extended into a diaper support position for supporting a associated dog diaper.
Figure 23:
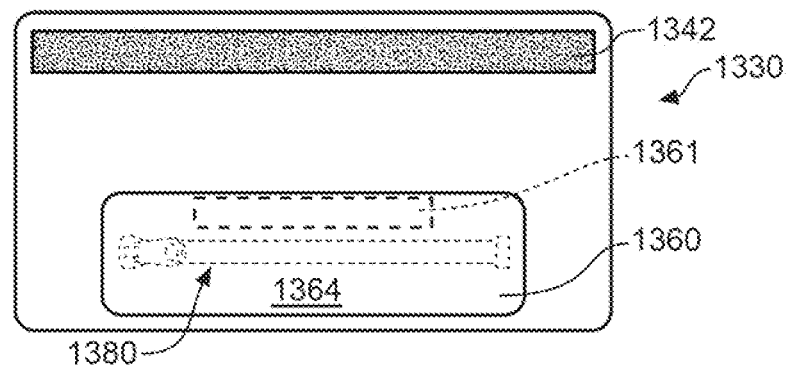
FIG. 23 is a bottom plane view of the diaper kit of FIG. 19.
Figure 24:
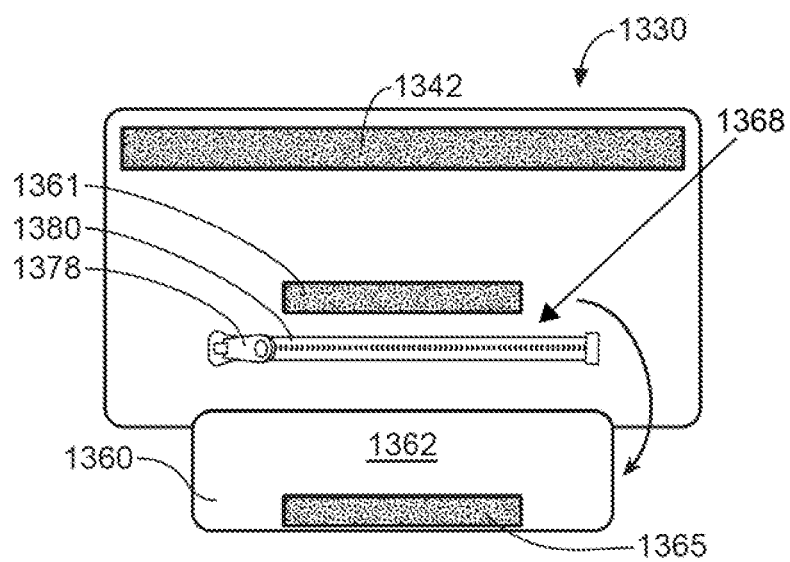
FIG. 24 is a bottom plane view of the diaper kit of FIG. 19, illustrating it primary support coupler folded forwardly into an open diaper engaging position.

Considering now the garment support arrangement 1330 in still greater detail with reference to FIGS. 20 and 22, the tail 1360 of the garment support arrangement 1330 has a diaper engaging surface area indicated generally at 1362 (FIG. 24). The diaper engaging surface area 1362 is provided with a primary support coupler arrangement 1365, which is composed of a plurality of hooks which may be arranged in a decorative design and which are adapted to engage and securely grip a top fabric surface of the diaper 40 so the tail 1360 is held in its open position 60 as best seen in FIG. 20 supporting the diaper 40 in its intended and desired animal protection position. In order to hold the tail 1360 in its closed position as best seen in FIG. 23, the garment support arrangement 1330 is provided with a tail fastener, indicated generally at 1361.

Figure 25:
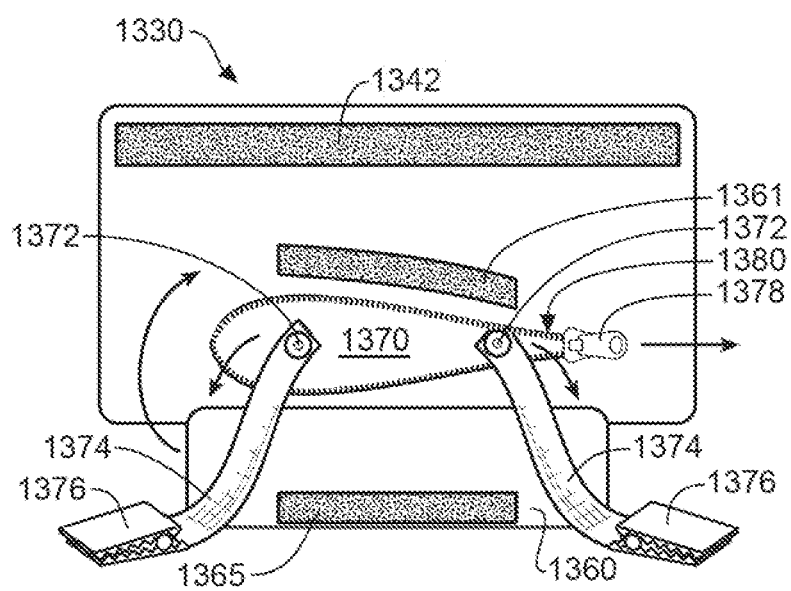
FIG. 25 is a bottom plane view of the diaper kit of FIG. 19, illustrating its storage compartment open exposing its secondary couplers ready for diaper engaging deployment.
Figure 26:
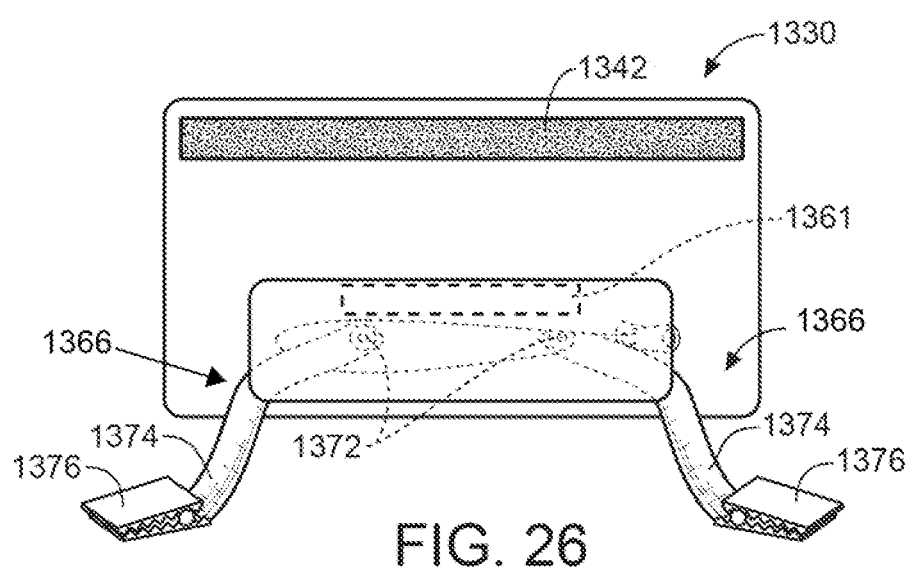
FIG. 26 is a bottom plane view of the diaper kit of FIG. 19, illustrating the primary support coupler in a closed position for helping to secure its secondary support couplers within the kit.

In a similar manner, the garment support arrangement 1330 is provided with a secondary support coupler arrangement 1380 (FIG. 24) which is concealed by the tail 1360 when it is disposed in its closed position as best seen in FIG. 23. The secondary support coupler arrangement 1380 generally includes a zippered pocket arrangement indicated generally at 1368 (FIG. 24) with an access opening 1370 (FIG. 25) with a zipper closure 1378. The access opening 1370 has disposed therein a pair of spaced apart tether pins, such as a tether pin 1372 having tethered thereto a secondary diaper coupler 1366 (FIG. 26). The secondary diaper coupler 1366 generally includes an elastic extension strap 1374 secured at its proximal end to the tether pin 1372 and having a diaper clip 1376 secured at its distal end. In this regard, the secondary diaper coupler 1366 may be released from the access opening 1370 and extended via the extension strap 1374 so the clip 1376 may be secured to the diaper 40 to hold or secure the diaper in its intended and desired animal protection position. When not in use, the secondary coupler 1366 is placed back into the access opening 1370 and enclosed therein by the zipper closure 1378 sealing the zippered pocket assembly 1368 until needed again for supporting or holding a diaper in place. It should be noted that the location of the garment support arrangement 1330 is selected so that it may easily and quickly be utilized to grippingly hold or secure the diaper 40 in its intended and desired animal protective position at a rear bodily area 14 of the animal 12, while at the same time being placed at a location where it can not be easily reached by the animal 12.

Because of its fabric construction, the garment support arrangement 1330 is adapted to be sewn, stitched, riveted or adhesively secured to the fabric surface area of the garment 1320 at about a distal end area 1394 thereof.

Referring now to FIG. 18, the novel and unique method 1400 of using the support garment 10 for holding or supporting a secondary animal protective garment, such as a diaper 40, to prevent the diaper 40 from sliding off the animal 12. In this regard, the support garment 10, via the garment support arrangement 30, effectively retains the diaper 40 in its intended desired animal protective position regardless of normal animal activity movement or because of excessive diaper weight caused when the absorbent material of the diaper 40 becomes saturated with the waste product of the animal 12.

The novel method of use 1400, begins at a start step 1402 and proceeds from the start step 1402 to a placing step 1404 where an animal owner, not shown, places the pet protection garment 10, on an animal 12 to be protected. The pet protection garment 10 in this regard is the primary animal protective garment 20 having disposed thereon the garment support arrangement 30. Next at another placing step 1406, the animal owner places a secondary animal protective garment 40, namely the animal diaper 40, on the animal 12. With the animal diaper 40 in place, the animal owner expects that any animal waste product eliminated from the animal 12 will be retained by the diaper 40 and will not be able to be deposited on the ground or floor in the surrounding environment whether the floor or ground is in a home residence, or on a footpath, or a sidewalk in a public or private location. However, to make absolutely certain that the diaper 40 does not accidental slip off the animal 12 due to normal animal movement or due to the absorbent material of the diaper 40 become excessively weighty due to the absorption of waste, the owner proceeds to a release or deployment step 1408.

At the release or deployment step 1408, the animal owner deploys a primary support coupler 52A from the garment support arrangement 30. In this regard, the owner opens the closure flap or tail 36 allowing it to be fully opened so the primary support coupler 52A carried by the closure flap 36 is able to engage with a fabric surface of the secondary animal protective garment 40. As will be explained hereinafter in greater detail, the garment support arrangement 30 may include a single support coupler or a plurality of support couplers, including like type couplers and unlike type couplers. For the moment however, for the purpose of describing this aspect of the unique and novel method of use 1400 only a single coupler, namely the primary support coupler 52A carried by the closure flap 36 will be described. In this regard, in order to facilitate the coupling of the primary animal protective garment 20 with the secondary animal protective garment 40, the closure flap 36 needs to have 1) a sufficient longitudinal length to extend from the primary animal protective garment 20 into an overlaying position on a desired fabric area of the diaper or secondary protective garment 40; and 2) a primary support coupler 52A with a set of loop fasteners or a set of hook fasteners that operates to provide a sufficient fastening or gripping force to securely hold the diaper 40. That is, the set of loop or hook fasteners must sufficiently grip and secure the diaper 40, so that it can not slide off the animal 12 because of normal animal activity movements or because of excessive weight caused when the absorbent material of the diaper 40 becomes saturated with the waste product of the animal 12.

Since there is great variation in the size of animals 12, in the size and fit of a primary animal protective garment 20 on an animal, and in the size, fit and fabric structure of a diaper, the closure flap 36 may not have a sufficient length to overlay the diaper 40 or the fabric structure of the diaper 40 may be such that it prevents the primary support coupler 52A from gripping its fabric structure, the process proceeds to a verifying step 1410, where the animal owner verifies that the primary support coupler 52A has in fact securely engaged the diaper 40.

The process continues to a decision step 1412, where the animal owner makes a determination that the diaper 40 is securely gripped and is being held in its intended and desired animal protection position. If the owner determines the diaper is not being securely held, the process advances to a go to secondary deployment step 1416 that will be described hereinafter in greater detail. On the other hand, if the animal owner determines that the diaper 40 is being securely held, the process proceeds to a go to a waiting step 1414.

Figure 18C:
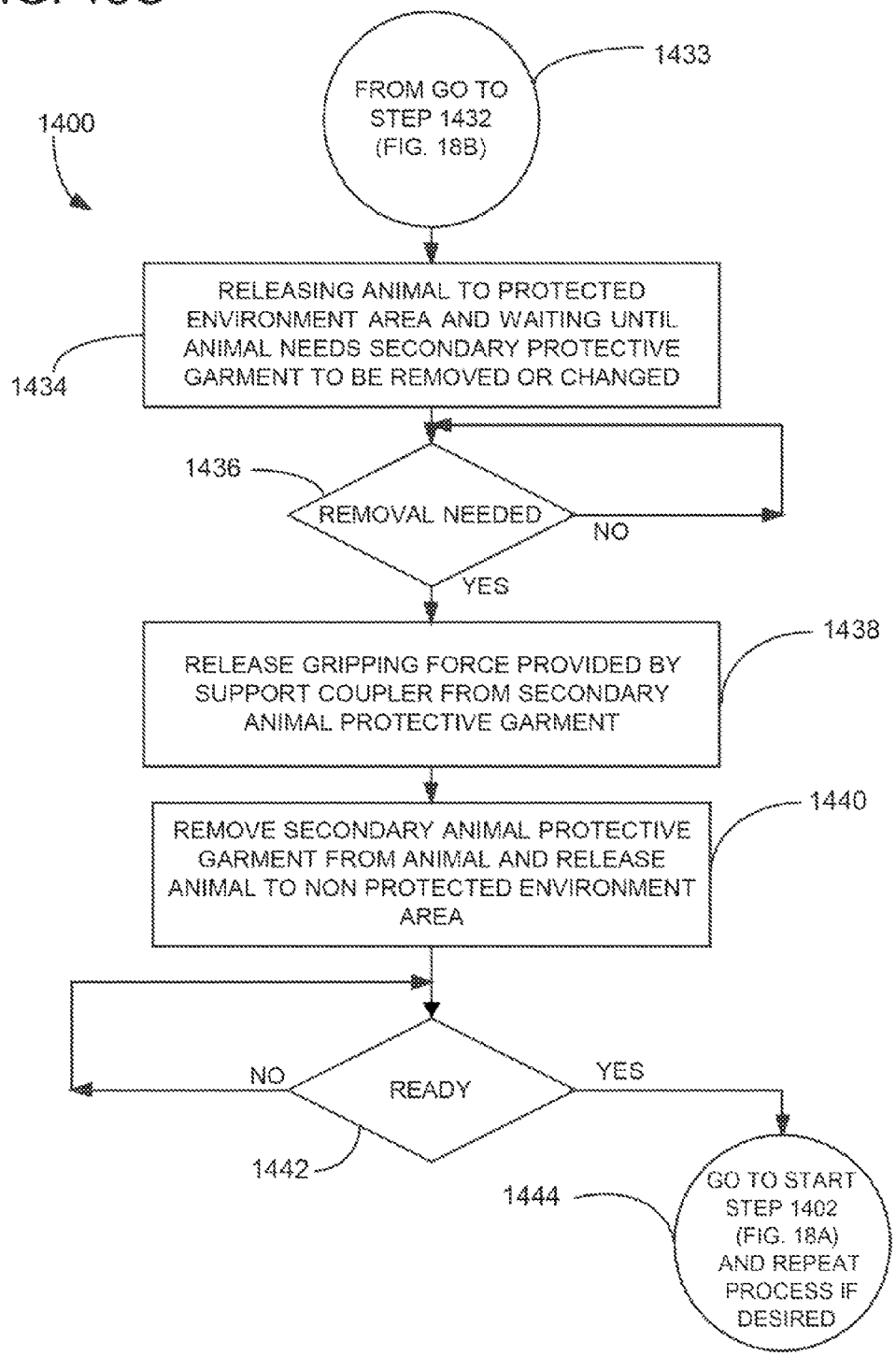

If the animal owner confirms that the primary support coupler 52A has firmly gripped the diaper 40 so the animal 12 may freely roam and move about within a protected environment, the process proceeds from step 1414 to step 1433 as best seen in FIG. 18C. In this regard, from step 1433, the process advances to a releasing and waiting step 1434, where the animal owner releases the animal 12 to a protected environmental area (not shown) and waits until the animal 12 needs the diaper 40 to be removed or changed. When released, should the animal 12 need to eliminate its bodily waste, it will be contained within the diaper 40 until such time as the animal owner intentionally removes the diaper 40 from the animal 12 being protected. This is described as a waiting step 1434 as best seen in FIG. 18C.

When the animal owner is ready to allow his or her animal 12 to be released to a non protected environment where the animal may eliminate its bodily waste products, the method proceeds to a removal decision step 1436 to determine if the diaper 40 needs to be removed from the animal 12. If not, the process simply waits at this decision step until such time as the diaper 40 needs to be changed or simply removed. In any event, if the diaper 40 needs to be changed or removed, the process advances to a releasing step 1438 where the animal owner releases the gripping forces applied to the diaper 40 via the garment support arrangement 30.

Next, the process advances to a removing step 1440, where the animal owner removes the diaper 40 from the animal and releases the animal to a non protected environment area, such as a runway, kennel area, or an non protected yarn area. The process then goes to a ready determination or decision step 1442 to determine when the animal owner is ready to have the animal 12 be returned to a protected environment. If the owner is not ready, the process repeats the ready decision step 1442 until the owner is ready. In any event, when the animal owner is ready, the process advances to a go to step 1444 which initiates a new process via a go to step 1444 which returns to step 1402 so the above-described process may be repeated again. If the owner determines that there is no longer any need for the animal 12 to be protected, the process ends when the owner removes the pet protection garment 10 from the animal 12 causing the novel method of use to be concluded.

Referring again to FIGS. 18A-B, if at decision step 1412, the animal owner determines that the primary support coupler 52A is not able to grippingly engage or secure the diaper 40, the process proceeds to a go to step 1416 for deploying a secondary support coupler, such as the support coupler 50. In this regard, the process advances from step 1416 to step 1418 and then to an opening step 1420. At the opening step 1420, the animal owner opens a secondary support coupler storage pocket and retrieves from the storage area of this storage pocket, a desired type of a secondary support coupler. In this regard, the secondary support coupler is selected from a group of support coupler consisting of fixed length support couplers and elastic support couplers that have the ability to stretch 2 to 8 times their non-stretched length. Such support couplers are provided with different types of fastening arrangements including a set of hook fasteners, a set of loop fasteners, an enlarged loop fastener, a clam shaped clip fastener, an alligator clip fastener, a slip clip fastener, and other conventional fasteners that can easily and quickly be deployed for gripping engagement with the diaper 40 to facilitate holding the diaper in its intended and desired animal protective position.

After retrieving the selected secondary support coupler 50 from the storage compartment, the process goes to an attaching step 1422. At the attaching step 1422, the animal owner attaches the selected secondary support coupler 50 to a male tether pin which is disposed in the deployment compartment. The attachment is done by simply pushing an associated female tether coupler, disposed at about a proximal end of the support coupler 50, onto the male tether pin.

When the secondary support coupler 50 is tethered to the pin, the process goes to a securing step 1424, where a fastener, such as an alligator clip fastener secured to the distal end of the support coupler 50 is opened and moved to the diaper 40 and released so that the fastener securely grips and holds the diaper 40. As mentioned earlier, other types of fasteners are fully contemplated by the present invention, so there is no intention of limiting the type of fastener to that of an alligator clip type fastener. Next, the process advances to an anchoring step 1426, where the animal owner moves the closure flap 36 back to its close position 62 where the closure flap 36 then anchors the tethered fastener or support coupler 50 so that it is securely held within the pocket of the garment support arrangement.

From the anchoring step 1426, the process advances to a determination step 1428, where the animal owner verifies that the support coupler 50 is securely anchored and is securely gripping the diaper 40 holding the diaper 40 in its intended and desired animal protective position. If the there is a problem with either the support coupler 50 being anchored or not securely gripping the diaper 40, the process returns to step 1426 and proceeds as previously described. If there is no problem with the support coupler 50 being anchored and securely gripping the diaper 40, the process goes to a go to step 1432 returning the process to step 1433 where the process continues from there as previously described.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant (s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as imitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an" and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. For example, rather than having as disclosed a neck-head junction with a replaceable head it is contemplated that a unitary ceramic neck-head configuration could be provided using a reverse Morse taper head-neck to collar interconnection allowing the unitary ceramic neck and head to be attached to a metallic collar have a short metallic neck extending therefrom to enable the reverse Morse taper connection. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the following claims.

PARTS LIST 10 a multi-purpose pet protection garment
12 an animal
14 a tail or rear bodily area of the animal
20 a primary animal protective garment (a sweater, a pressure wrap, etc)
30 a secondary garment support arrangement
36 a tail forming an integral part of the primary animal protective garment
36A a top diaper engaging surface area
36B a bottom primary protective garment engaging surface area
40 a secondary animal protection garment (a diaper or shield)
40S a diaper strap
50 a secondary support coupler
52A a primary support coupler arrangement
52B a secondary support coupler arrangement
60 an open position of the secondary garment support arrangement
62 a closed position of the secondary garment support arrangement
90 a top fabric surface area of the garment 20
94 a distal end area of the primary animal protective garment 20
110 a self contained garment support kit
120 a primary animal protective garment
130 a garment support arrangement
131 an adhesive backing
132 a base or pocket unit
133 a pocket fastener
136 a closure nap
136A a top surface area of the closure flap
136B a bottom surface area of the closure flap
138 a top surface floor area of the pocket unit
152A a primary support coupler
152B a secondary support coupler
190 a top fabric surface area
194 a distal boundary end of the pocket unit
210 another self contained garment support kit
230 a garment support arrangement
232 a base or pocket unit
233 a closure fastener
234 a primary support coupler (carried by closure flap 236)
235 a closure flap fastener
236 a diaper engaging closure flap
236A a top or a diaper engaging surface area
236B a bottom or a base unit engaging surface area
237 a coupler engaging closure flap
237A an upper surface area of the closure flap 237
239 a fastener
240 a storage compartment (carried by closure flap 237)
242 a floor area of the pocket unit 232
250 a secondary support coupler
252 a male tether pin
253 a female pin receiving component
254 a clam shaped clip
294 a distal end area of the pocket unit 232
310 a multi-purpose pet protection garment
330 a garment support arrangement
332 a pocket area
333 a fastener
335 a fastener
336 a closure flap
336A an outside surface area
336B an inside surface area
342 a floor area of the pocket area 332
350 an adjustable fixed length strap coupler
352 tether pins
360 an adjustable elastic strap coupler
370 an elastic band type secondary coupler
380 an elastic Y-band type coupler

| | |
|---|---|
| 381 an extension arm | 1376 a clip |
| 382 an extension arm | 1378 a zipper closure |
| 390 an elastic loop coupler | 1380 a secondary support coupler arrangement |
| 410 a pet protection garment | 1390 an imaginary lateral line |
| 430 a garment support arrangement | 1394 a distal end area |
| 432 a base or utility pocket | 1400 method of use |
| 433 a fastener | 1402 a start step |
| 436 a closure flap | 1404 a placing step |
| 436A an outside surface area | 1406 another placing step |
| 436B an inside surface area | 1408 a deployment step |
| 438 a secondary support coupler storage compartment | 1410 a verifying step |
| 442 a detent | 1412 a decision or determination step |
| 444 a tether pad | 1414 go to waiting step |
| 450 a secondary support coupler | 1416 go to secondary deploying step |
| 466 a zipper pocket assembly | 1418 a from step |
| 481 inside pocket layer | 1420 an opening step |
| 482 an outside pocket layer | 1422 an attaching step |
| 483 a stitch line | 1424 a securing step |
| 484 a stitch line | 1426 an anchoring step |
| 485 a stitch line | 1428 a determination step |
| 486 an access opening | 1432 a go to step |
| 488 a zipper closure | 1433 a from step |
| 510 a pet protection garment | 1434 a releasing step |
| 530 a garment support arrangement | 1436 a decision step |
| 532 a backup storage compartment | 1438 a releasing step |
| 536 a closure flap | 1440 a removing step |
| 538 a backup storage compartment | 1442 a decision step |
| 544 a tether pad | 1444 a go to step |
| 550 a secondary support coupler | |

We claim:

1. Multi-functional animal apparel for use with a disposable diaper that substantially covers the hindquarter of an animal, comprising:

an elongated animal garment provided with a proximal end portion for substantially covering a chest body portion of an animal and a distal end portion for substantially covering from the chest body portion of the animal to at least a midsection portion of the animal without interfering with waste product discharge from the animal;

a support arrangement disposed at about said distal end portion of the elongated animal garment to conceal for deployment a plurality of diaper couplers to help grip, secure and maintain the disposable diaper in an intended animal protective position on the animal; and wherein said support arrangement is a closable receptacle holding pocket, said pocket including a closure flap moveable between an open position and a close position, said closure flap having a sufficient width dimension and length dimension when disposed in said open position for carrying at least one additional diaper coupler into an overlaying relationship with the disposable diaper to facilitate positioning said at least one additional diaper coupler in a proper location to help to further grip, secure and maintain the disposable diaper in the intended animal protective position on the animal.

2. Multi-functional animal apparel according to claim 1, where said at least one additional diaper coupler is composed of a plurality of loops or a plurality of hooks.

3. Multi-functional animal apparel according to claim 2, wherein said plurality of loops or said plurality of hooks are arranged in a decorative design to provide said closure flap with an ornamental feature.

4. Multi-functional animal apparel for use with a disposable diaper that substantially covers the hindquarter area of an animal, comprising:

an article of animal clothing, said article of animal clothing having a proximal end portion for substantially covering a front body area of the animal and a distal end portion for substantially covering at least a midsection body area of the animal without interfering with waste product discharge from the animal; and a closable pocket disposed at about said distal end portion of the article of animal clothing to conceal and store for deployment as needed at least one diaper coupler to grip, secure and help maintain the disposable diaper in an intended animal protective position for capturing and collecting waste product discharge from the animal and for carrying and deploying at least another diaper coupler into an overlaying relationship with the disposable diaper to further grip, secure and help maintain the disposable diaper in an intended animal protective position for capturing and collecting waste product discharge from the animal.

5. Multi-functional animal apparel according to claim 4, wherein said closable pocket is further disposed on a top side of said distal end portion of the article of animal clothing to enable a closure flap to open rearwardly forming a garment tail with a sufficient length to be disposed in an overlaying relationship with the disposable diaper.

6. Multi-functional animal apparel according to claim 5, wherein said closable pocket is provided with anchoring means for tethering therefrom said at least one diaper coupler.

7. Multi-functional animal apparel according to claim 6, wherein said at least one diaper coupler includes like-type couplers and unlike-type couplers.

8. Multi-functional animal apparel according to claim 7, wherein said like-type couplers include fixed length couplers, and wherein said unlike-type couplers include couplers selected from a group of diaper couplers including: variable length diaper couplers, elastic support diaper couplers, clam shell diaper couplers, alligator clip diaper couplers, draw string diaper couplers, Y-band diaper couplers and hook and loop diaper couplers.

9. Multi-functional animal apparel according to claim 6, wherein said closable pocket further includes a storage compartment.

10. Multi-functional animal apparel according to claim 9, wherein said storage compartment has sufficient space therein for storing a packaged animal diaper, said packaged animal diaper being available for use when the first mentioned disposable diaper is spent and used capturing and collecting waste product discharge from the animal.

11. Multi-functional animal apparel according to claim 9, wherein said storage compartment has sufficient space therein for storing said at least one diaper coupler.

12. Multi-functional animal apparel according to claim 6, wherein said closable pocket is composed of a fabric material.

13. Multi-functional animal apparel according to claim 4, wherein said closable pocket is decorative with an aesthetic appearance selected to be coordinated in appearance to said article of animal clothing.

14. Multi-functional animal apparel according to claim 4, wherein said closable pocket is stitched to the article of clothing.

15. Multi-functional animal apparel according to claim 14, further comprising:
 a closure flap is stitched to said closable pocket at about a distal boundary end edge area thereof so said closure flap is moveable about a distal end of said closable pocket from a closed pocket position to an open pocket position for diaper engaging purposes;
 wherein said closure flap has a sufficient length dimension and a sufficient width dimension to overlay a substantial top surface proximal end area of the diaper when said closure flap is disposed in an open pocket position.

16. Multi-functional animal apparel according to claim 4, wherein said at least one diaper coupler includes like-type couplers and unlike-type couplers, and wherein said like-type couplers include fixed length couplers.

17. Multi-functional animal apparel according to claim 16, wherein said unlike-type couplers include variable length diaper couplers, elastic diaper couplers, clam shell couplers, alligator clip diaper couplers, draw string diaper couplers, and hook and loop diaper couplers.

\* \* \* \* \*